United States Patent [19]

Cook et al.

[11] 4,138,555

[45] Feb. 6, 1979

[54] (6R,7R)-7-[2-ARYL-2-(ETHERIFIED OXIMINO)ACETAMIDO]-3-CARBAMOYLOXYMETHYLCEPH-3-EM-4-CARBOXYLIC ACID 1-OXIDES

[75] Inventors: Martin C. Cook, Liverpool; Gordon I. Gregory, Chalfont St. Peter; Janice Bradshaw, Harrow, all of England

[73] Assignee: Glaxo Laboratories, Limited, Greenford, England

[21] Appl. No.: 852,808

[22] Filed: Nov. 18, 1977

Related U.S. Application Data

[60] Continuation of Ser. No. 685,628, May 12, 1976, abandoned, which is a division of Ser. No. 497,113, Aug. 13, 1974, Pat. No. 3,974,153, which is a continuation-in-part of Ser. No. 413,970, Nov. 8, 1973, Pat. No. 3,966,717, which is a continuation-in-part of Ser. No. 304,524, Nov. 7, 1972, Pat. No. 3,971,778, which is a continuation-in-part of Ser. No. 252,666, May 12, 1972, abandoned.

[30] Foreign Application Priority Data

May 14, 1971 [GB] United Kingdom ............... 15082/71
Oct. 1, 1971 [GB] United Kingdom ............... 45884/71
May 12, 1972 [GB] United Kingdom ............... 45884/72

[51] Int. Cl.$^2$ ............................................ C07D 501/20
[52] U.S. Cl. ...................................... 544/22; 544/16; 424/246
[58] Field of Search ......................................... 544/22

[56] References Cited

FOREIGN PATENT DOCUMENTS 2223375 11/1972 Fed. Rep. of Germany.

Primary Examiner—Nicholas S. Rizzo
Attorney, Agent, or Firm—Bacon & Thomas

[57] ABSTRACT

Cephalosporin antibiotics in which the 7β-acylamido group has the structure

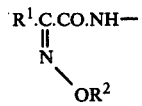

where $R^1$ is a furyl, thienyl or phenyl group and $R^2$ is a $C_1$-$C_4$ alkyl, $C_3$-$C_7$ cyclcoalkyl or phenyl group and in which the 3-position substituent is a carbamoyloxymethyl group possess a particularly valuable combination of properties, exhibiting high antibacterial activity against a broad range of gram positive and gram negative organisms, paticularly high stablity to β-lactamases produced by various organisms, and stability in vivo. The compounds are syn isomers or exist as mixtures of syn and anti isomers containing at least 90% of the syn isomer. Particularly important compounds of this type are (6R,7R)-3-carbamoyloxymethyl-7-[2-(fur-2-yl)-2-methoxyiminoacetamido]ceph-3-em-4-carboxylic acid (syn isomer) and its non-toxic derivatives, e.g. the sodium salt.

3 Claims, No Drawings

(6R,7R)-7-[2-ARYL-2-(ETHERIFIED OXIMINO)ACETAMIDO]-3-CARBAMOYLOXYMETHYLCEPH-3-EM-4-CARBOXYLIC ACID 1-OXIDES

CROSS REFERENCE TO RELATED APPLICATIONS

This application is a continuation of copending application Ser. No. 685,628, filed May 12, 1976, and now abandoned, which is in turn a division of application Ser. No. 497,113, filed Aug. 13, 1974, and now U.S. Pat. No. 3,974,153, which is in turn a continuation-in-part of application Ser. No. 413,970, filed Nov. 8, 1973, and now U.S. Pat. No. 3,966,717, which is in turn a continuation-in-part of application Ser. No. 304,524, filed Nov. 7, 1972, and now U.S. Pat. No. 3,971,778, which is in turn a continuation-in-part of application Ser. No. 252,666 filed May 12, 1972, and now abandoned.

This invention is concerned with improvements in or relating to antibiotics of the cephalosporin series.

The cephalosporin compounds in this specification are named with reference to "cepham" after *J. Amer. Chem. Soc.*, 1962, 84, 3400, the term "cephem" referring to the basic cepham structure with one double bond.

Many cephalosporin compounds possessing a degree of antibacterial activity are known in the art, these compounds possessing $\Delta^3$ unsaturation and ordinarily being substituted at the 3-position by a methyl or substituted methyl group and at the 7β-position by an acylamido group. It is now well recognised that the antibiotic properties of a particular ceph-3-em-4-carboxylic acid are predominantly controlled by the nature of both the 7β-acylamido group thereof and the 3-position substituent which the compound carries; considerable research has been undertaken to find combinations of such groups which will yield antibiotics with particular properties.

Cephalosporin antibiotics are widely used in the treatment of diseases caused by pathogenic bacteria in human beings and animals, for example in the treatment of diseases caused by bacteria which are resistant to other antibiotics such as penicillin compounds and in the treatment of penicillin-sensitive patients. In many applications it is desirable to employ a cephalosporin antibiotic which exhibits activity against both gram positive and gram negative microorganisms, and a significant amount of research has been directed to the development of improved broad spectrum cephalosporin antibiotics.

The practical utility of a significant number of known commercial and experimental cephalosporin antibiotics is limited by their relatively high susceptibility to the β-lactamases which are produced by many bacteria. A desirable property of a broad spectrum cephalosporin antibiotic is therefore that it should exhibit substantial resistance to β-lactamases, including those produced by gram negative microorganisms.

A further difficulty with many cephalosporin antibiotics intended for therapeutic applications is that they are subject to degradation in vivo. Thus a significant number of known cephalosporin antibiotics have been found to suffer the disadvantage that following administration they are deactivated, often rapidly, by enzymes (e.g. esterases) present in the body.

As a result of prolonged studies of numerous cephalosporin compounds we have now found a class of cephalosporin antibiotics having a particular combination of 7β-acylamido group and 3-position substituent which endows the compounds with good broad spectrum activity coupled with the above-described desiderata of high β-lactamase stability and good stability in vivo. These compounds are characterised in that the 7β-acylamido group is a 2-aryl-2-(etherified oxyimino)acetamido group which is substantially in the syn configuration (as hereinafter defined) and that the 3-substituent is a carbamoyloxymethyl group.

According to one aspect of the present invention, therefore, there are provided antibiotic compounds of the general formula

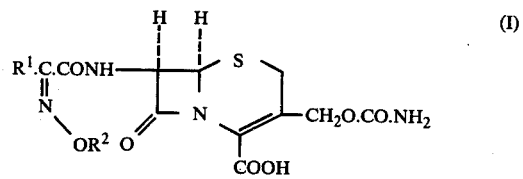

(where $R^1$ represents a furyl, thienyl or phenyl group and $R^2$ represents a $C_1$-$C_4$ alkyl group, a $C_3$-$C_7$ cycloalkyl group or a phenyl group) and non-toxic derivatives of these acids, the compounds being syn isomers or existing as mixtures of syn and anti isomers containing at least 90% of the syn isomer. Most preferably the compounds are the syn isomers essentially free from the corresponding anti isomers.

The compounds of the invention are defined as having the syn (cis) isomeric form as regards the configuration of the group $OR^2$ with respect to the carboxamido group. In this specification the syn configuration is structurally denoted thus:

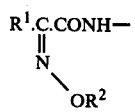

The syn configuration is assigned on the basis of the work of Ahmad and Spenser as reported in *Can. J. Chem.* 1961, 39, 1340.

The term "non-toxic" as applied to derivatives of the compounds of the invention means those derivatives which are physiologically acceptable in the dosage at which they are administered. Such derivatives may include, for example, salts, biologically acceptable esters, 1-oxides and solvates (especially hydrates) of the compounds.

Salts which may be formed from the compounds of general formula I include inorganic base salts such as alkali metal (e.g. sodium and potassium), alkaline earth metal (e.g. calcium) and organic base (e.g. procaine, phenylethylbenzylamine, dibenzylethylenediamine, ethanolamine, diethanolamine, triethanolamine and N-methylglucosamine) salts. The salts may also comprise resinates, formed with, for example, a polystyrene resin or cross-linked polystyrene divinylbenzene copolymer resin containing amino or quaternary amino groups.

Where $R^1$ in general formula I is a furyl group it may be fur-2-yl or fur-3-yl and when it is a thienyl group it may be thien-2-yl or thien-3-yl. Preferably the group $R^1$ is a fur-2-yl group.

As indicated above, the group $R^2$ in formula I represents an alkyl group containing 1–4 carbon atoms, e.g. a methyl, ethyl or t-butyl group; a cycloalkyl group containing 3–7 carbon atoms, e.g. a cyclopentyl group; or a phenyl group.

The compounds of the invention, as indicated above, possess a particularly valuable combination of properties, exhibiting high antibacterial activity against a broad range of gram-positive and gram-negative organisms. The breadth of the activity spectrum is enhanced by the particularly high stability of the compounds to β-lactamases produced by various gram-negative organisms. The compounds show the advantageous property of good stability in vivo, particularly to esterases.

The properties possessed by the compounds according to the invention render them useful in the treatment of a variety of diseases caused by pathogenic bacteria in human beings and animals.

An important compound according to the invention is (6R,7R)-3-carbamoyloxymethyl-7-[2-(fur-2-yl)-2-methoxyiminoacetamido]ceph-3-em-4-carboxylic acid (syn isomer), which has the formula

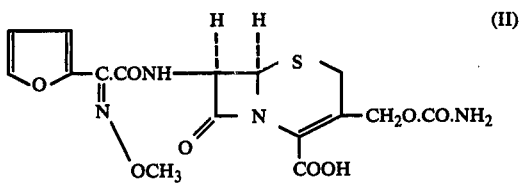

and which is conveniently in the form of an alkali metal salt, especially the sodium salt. This compound is active against a wide range of gram-positive and gram-negative microorganisms, e.g. *Staphylococci* including *Staphylococcus aureus*, *Streptococcus pyogenes* and *Streptococcus vilidans*, *Diplococcus pneumoniae*, *Haemophilus influenzae*, *Neisseria* and *Clostridia* species, *Escherichia coli*, *Klebsiella*, *Proteus* and *Enterobacter* species, as evidenced by both in vitro and in vivo tests. The compound exhibits good in vitro activity at inoculum levels as high as $10^7$ organisms/ml and possesses particularly high in vitro activity against strains of *Haemophilus influenzae*, *Neisseria gonorrhoeae* and *Neisseria meningitidis*. The compound possesses very high stability of β-lactamases produced by a range of gram-negative organisms as evidenced by, for example, its in vitro activity against various β-lactamase-producing strains of *Escherichia*, *Enterobacter* and *Klebsiella* species. The compound is resistant to the action of mammalian esterases and is thus stable in the bodies of humans and animals as evidenced by high levels of recovery of unchanged compound in the urine. Furthermore, the compound gives high serum levels following parenteral administration to both human and animal subjects, while exhibiting low serum binding.

Use of highly soluble base salts (e.g. alkali metal salts such as the sodium salt) of the compound is of advantage in therapeutic applications because of their rapid distribution in the body on administration by injection.

We have found that sodium (6R,7R)-3-carbamoyloxymethyl-7-[2-(fur-2-yl)-2-methoxyiminoacetamido]-ceph-3-em-4-carboxylate (syn isomer) occurs in a number of different crystalline forms, including solvates, all of which are embraced by the present invention.

The sodium salt is most conveniently prepared by contacting a solution of the compound (II) in a polar organic solvent (e.g. dimethylacetamide), a mixture of such solvents (e.g. dimethylacetamide/acetone or dimethylformamide/industrial methylated spirits) or an aqueous polar organic solvent system (e.g. aqueous acetone) with a slight molar excess of sodium 2-ethylhexanoate dissolved in a suitable organic solvent (e.g. an alkanol such as ethanol, a ketone such as acetone, or a chlorinated hydrocarbon such as methylene chloride an ester such as ethyl acetate, an ether such as dioxan), conveniently at ambient temperature, and then collecting the precipitated salt, if desired after cooling the solution (e.g. to 4° C.).

Where substantially anhydrous solvents are employed in this process, Form I sodium (6R,7R)-3-carbamoyloxymethyl-7-[2-(fur-2-yl)-2-methoxyiminoacetamido]ceph-3-em-4-carboxylate (syn isomer) is obtained, this material containing about 1.5% water. Where the solvent system contains more than about 2% of water, however, Form II salt is obtained, this normally containing about 2% water. Where the solvent system contains more than about 60% dioxan, Form III salt is normally obtained, this material comprising a dioxan solvate containing about 1 mole of dioxan, although Form II salt may be obtained if a water wet solvent system is used at elevated temperature (e.g. 60°–80° C.). Crystallisation of amorphous freeze-dried sodium (6R,7R)-3-carbamoyloxymethyl-7-[2-(fur-2-yl)-2-methoxyiminoacetamido]ceph-3-em-4-carboxylate (syn isomer) from appropriate dry, water-containing or dioxan-rich solvent systems similarly yields Form I, Form II or Form III salt respectively.

Exposure of Form I salt to water vapour (e.g. at 75% relative humidity) causes the salt to absorb further water and undergo a change of crystalline form leading generally to Form IV salt. The resulting material contains about 4% water (i.e. about 1 mole) and is believed to be a hydrate. This change is reversible, so that Form IV salt may be converted to Form I salt by, for example, drying in vacuo over a desiccating agent such as phosphorus pentoxide. Form II salt does not absorb further water when exposed to water vapour, but may be converted to Form I salt by heating (e.g. for about 5 minutes) a suspension of Form II material in nearly boiling methanol.

Form III salt obtained by reaction of the compound (II) and sodium 2-ethylhexanoate in dioxan-rich solvent systems as described above is normally precipitated as a gel, which may be dried in vacuo to give a solid having very low bulk density and exhibiting little or no crystallinity. Crystalline Form III salt may, however, be obtained by treating an aqueous solution of the sodium salt with a substantial excess (e.g. about 8 volumes) of dioxan, if desired together with a minor proportion of ethanol, collecting the resulting white, needle-shaped crystals, conveniently after cooling to a reduced temperature (e.g. 4° C.), washing the product with dioxan and then drying the crystals (e.g. in vacuo at 20° C.).

Form III salt is hygroscopic and on exposure to water vapour (e.g. at 75% relative humidity) loses all the dioxan present and forms Form IV material, which may then be dried (e.g. over phosphorus pentoxide) to give Form I salt. If crystalline Form III material is treated in this way, the crystal habit of the product appears to be retained throughout the sequence of transformations. Form III salt may also be converted to Form I salt by heating a suspension of Form III material in nearly boiling methanol; this transformation does result in loss of crystallinity where crystalline Form III material is used.

The four forms of sodium (6R,7R)-3-carbamoyloxymethyl-7-[2-(fur-2-yl)-2-methoxyiminoacetamido]-ceph-3-em-4-carboxylate (syn isomer) described above are characterised by the following X-ray powder patterns (d-spacings and intensities) and IR spectroscopic data:

X-ray powder patterns
Camera - Debye-Scherrer, radius 114.6 mm
Radiation - Copper $K_d$ = 1.5418 Å
Intensities (I) by visual comparison with calibrated standard Form I

| d | I | d | I |
|---|---|---|---|
| 8.33 | 80 | 3.05 | 4 |
| 7.44 | 4 | 2.93 | 14 (broad) |
| 6.85 | 45 | 2.72 | 8 ⎫ poorly |
| 6.38 | 5 | 2.69 | 10 ⎬ re-solved |
| 5.86 | 4 | 2.57 | 9 |
| 5.36 | 4 | 2.47 | 6 |
| 4.82 | 100 | 2.40 | 10 |
| 4.56 | 35 | 2.35 | 10 |
| 4.36 | 6 | 2.26 | 4 |
| 4.19 | 40 | 2.20 | 3 |
| 3.95 | 26 | 2.11 | 8 (broad) |
| 3.82 | 24 | 2.04 | 3 |
| 3.62 | 28 | 1.94 | 4 |
| 3.47 | 28 | 1.89 | 5 |
| 3.32 | 10 | 1.82 | 6 (broad) |
| 3.19 | 10 | 1.77 | 2 |

Form II

| d | I | d | I |
|---|---|---|---|
| 8.78 | 60 | 3.49 | 14 |
| 7.81 | 9 | 3.07 | 6 (broad) |
| 6.65 | 25 | 2.91 | 8 |
| 4.68 | 100 (broad) | 2.77 | 6 |
| 4.45 | 10 | 2.32 | 3 (broad) |
| 4.20 | 10 | 2.19 | 2 |
| 3.76 | 20 (broad) | 2.08 | 2 |

Form III

| d | I | d | I |
|---|---|---|---|
| 14.98 | 60 | 4.29 | 20 |
| 12.95 | 40 | 4.16 | 100 |
| 10.16 | 20 | 3.81 | 25 (broad) |
| 8.23 | 45 | 3.60 | 20 |
| 7.52 | 5 | 3.47 | 5 |
| 6.61 | 65 | 3.32 | 10 |
| 6.08 | 3 | 3.26 | 30 |
| 5.57 | 20 | 3.13 | 17 (broad) |
| 4.98 | 40 | 2.43 | 10 |
| 4.73 | 60 | 2.15 | 15 |

Form IV

| d | I | d | I |
|---|---|---|---|
| 8.85 | 70 | 3.75 | 35 |
| 7.80 | 6 | 3.10 | 1 |
| 7.15 | 25 | 2.93 | 4 |
| 6.01 | 20 | 2.76 | 12 |
| 5.06 | 18 | 2.62 | 1 |
| 4.65 | 100 | 2.41 | 2 |
| 4.30 | 25 | 2.30 | 3 |
| 4.01 | 25 | | |

IR Spectra
Spectrometer - Perkin-Elmer 521, range 4000 - 650 cm$^1$
Spectra recorded for Nujol mulls (bands associated with Nujol are excluded)

Form I

| | | | |
|---|---|---|---|
| 3520 w | *1590 s | 1262 m | 1004 m |
| 3460 m | 1556 m | 1248 m | 978 m |
| 3370 m | 1534 s | 1170 m | 918 w |
| 3265 s | 1480 m | 1152 m | 882 s |
| 1770 sh | 1410 s | 1134 w | 878 sh |
| 1752 s | 1400 s | 1112 m | 838 w |
| 1706 s | 1338 s | 1076 m | 814 w |
| 1660 s | 1328 s | 1054 sh | 790 w |
| 1620 s | 1284 m | *1042 s | 778 w |
| | | | 754 m |

Form II

| | | | |
|---|---|---|---|
| 3526 m | 1544 s | 1152 m | 920 w |
| 3492 w | 1478 m | 1142 m | 882 m |
| *3364 m | 1412 s | 1112 m | 878 w |
| 3250 m | 1398 s | 1080 m | 840 w |
| 1758 s | 1332 s | 1058 m | 818 w |
| 1695 s | 1284 m | *1045 m | 792 w |
| 1665 s | 1268 m | 1005 m | 752 m |
| 1642 sh | 1240 m | 980 m | |
| 1624 s | 1172 m | 954 w | |

-continued
IR Spectra

Form III

| | | | |
|---|---|---|---|
| 3465 m | 1532 s | 1155 m | 820 w |
| 3415 m | 1482 m | *1124 s | 800 w |
| 3345 m | 1412 s | 1078 m | 790 w |
| 3275 m | 1395 s | *1058 s | 768 m |
| 3200 m | 1326 s | 1048 s | 748 m |
| 1780 s | 1285 m | 1014 m | |
| 1702 s | 1260 m | 985 m | |
| 1660 s | 1230 m | 938 w | |
| 1632 m | 1225 m | 888 m | |
| 1618 s | 1196 w | 878 s | |
| 1552 m | 1180 m | 836 w | |

Form IV

| | | | | |
|---|---|---|---|---|
| 3585 w | 1594 s | 1264 m | 1008 m | 788 w |
| 3520 w | 1555 m | 1240 m | 980 m | 752 m |
| 3370 m | 1540 m | 1172 w | 956 w | |
| *3260 s | 1478 m | 1152 m | 920 w | |
| 1758 s | 1410 s | 1114 w | 882 m | |
| 1712 s | 1400 s | 1078 m | 878 w | |
| 1664 s | 1330 s | 1058 m | 838 w | |
| 1620 s | 1285 m | 1042 m | 818 w | |

Key
s = strong
sh = shoulder
m = medium
w = weak
*denotes bands characteristic of each crystalline form.

Where insoluble salts of the compound (I) are desired in a particular application, for example for use in depot preparations, such salts may be formed in conventional manner, for example with appropriate organic amines.

According to a further aspect of the invention we provide a process for the preparation of an antibiotic compound of formula I (as hereinbefore defined) and non-toxic derivatives (e.g. salts, esters, 1-oxides and solvates) thereof which comprises either (A) condensing a compound of general formula

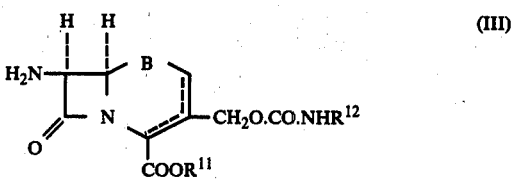

(III)

(wherein B is $> S$ or $> S \rightarrow O$; $R^{11}$ is hydrogen or a carboxyl blocking group, e.g. the residue of an ester-forming aliphatic or araliphatic alcohol or an ester-forming phenol, silanol or stannanol, or a symmetrical or mixed anhydride group derived from an appropriate acid; $R^{12}$ is hydrogen or an N-protecting group, e.g. an acyl group, especially a lower alkanoyl group such as acetyl, a halo-substituted lower alkanoyl group such as mono-, di- or tri-chloroacetyl, or a chlorosulphonyl group; and the dotted line bridging the 2-,3- and 4-positions of the molecule indicates that the compound may be a ceph-2-em or a ceph-3-em compound) or a derivative thereof (e.g. an acid addition salt formed with, for example, a mineral acid such as hydrochloric, hydrobromic, sulphuric, nitric or phosphoric acid or an organic acid such as methane sulphonic or toluene p-sulphonic acid or an N-silyl derivative) with an acylating agent corresponding to the acid

(IV)

(wherein $R^1$ and $R^2$ have the above-defined meanings) or with an acylating agent corresponding to an acid which is a precursor for the acid (IV); or (B) reacting a compound of the formula

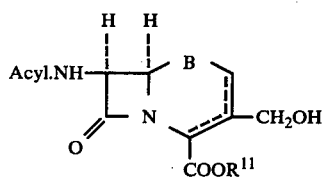  (V)

(wherein Acyl is the group

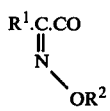

in which $R^1$ and $R^2$ have the above-defined meanings or a precursor therefor, and B, $R^{11}$ and the dotted line have the above-defined meanings) with a carbamoylating agent serving to form a carbamoyloxymethyl group or an N-protected carbamoyloxymethyl group at the 3-position; whereafter, if necessary and/or desired in each instance, any of the following reactions (C), in any appropriate sequence are carried out:

(i) conversion of a precursor for the desired

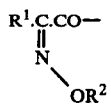

group into that said group, (ii) conversion of a $\Delta^2$ isomer into the desired $\Delta^3$ isomer, (iii) removal of any carboxyl blocking or N-protecting groups, and (iv) reduction of a cephalosporin sulphoxide product to yield the corresponding sulphide; and finally (D) recovering the desired compound of formula I, if necessary after separation of syn and anti isomers and if desired after conversion of the compound to a non-toxic derivative thereof.

Non-toxic derivatives of the compounds of formula I may be formed in any convenient way, for example according to methods well known in the art. Thus, for example, base salts may be formed by reaction of the cephalosporin acid with sodium or potassium 2-ethylhexanoate. Biologically acceptable ester derivatives may be formed using conventional esterifying agents. 1-Oxides may be formed be treatment of the corresponding cephalosporin sulphide with an appropriate oxidising agent, for example with a peracid such as metaperiodic acid, peracetic acid, monoperphthalic acid or m-chloroperbenzoic acid, or with t-butyl hypochlorite conveniently in the presence of a weak base such as pyridine.

Compounds of formula I may conveniently be prepared by condensing a compound of formula III with an acylating agent comprising an acid halide, particularly an acid chloride or bromide, corresponding to the acid (IV). Such acylation may be effected at temperatures of from $-50°$ to $+50°$ C., preferably $-20°$ to $+30°$ C. The acylation may be effected in aqueous or non-aqueous media.

Acylation with an acid halide may be effected in the presence of an acid binding agent (e.g. a tertiary amine such as triethylamine or dimethylaniline, an inorganic base such as calcium carbonate or sodium bicarbonate, or an oxirane, preferably a lower-1,2-alkylene oxide such as ethylene oxide or propylene oxide) which serves to bind hydrogen halide liberated in the acylation reaction.

The free acid form of a compound of formula IV may itself be used as the acylating agent. Such acylations are desirably conducted in the presence of, for example, a carbodiimide such as N,N'-diethyl-, dipropyl- or diisopropylcarbodiimide, N,N'-dicyclohexylcarbodiimide, or N-ethyl-N'-γ-dimethylaminopropylcarbodiimide; a carbonyl compound such as carbonyldiimidazole; or an isoxazolinium salt such as N-ethyl-5-phenylisoxazolinium-3'-sulphonate or N-t-butyl-5-methylisoxazolinium perchlorate. The condensation reaction is desirably effected in an anhydrous reaction medium, e.g. methylene chloride, dimethylformamide or acetonitrile.

Acylation may also be effected with other amide-forming derivatives of the free acid (IV) such as, for example, a symmetrical anhydride or a mixed anhydride, e.g. with pivalic acid or formed with a haloformate such as a lower alkyl haloformate. The mixed or symmetrical anhydrides may be generated in situ. Thus, for example, a mixed anhydride may be generated using N-ethoxycarbonyl-2-ethoxy-1,2-dihydroquinoline. Mixed anhydrides may also be formed with phosphorus acids (for example phosphoric or phosphorus acids), sulphuric acid or aliphatic or aromatic sulphonic acids (for example p-toluenesulphonic acid).

If desired, one may prepare a compound of formula

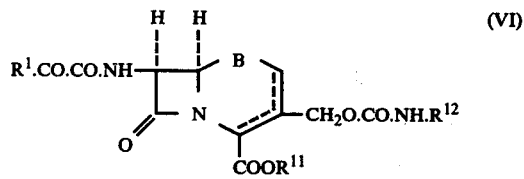  (VI)

(wherein B, $R^1$, $R^{11}$, $R^{12}$ and the dotted line have the above-defined meanings) by condensation of a compound of formula III with an acylating agent corresponding to a precursor acid of the formula

  (VII)

(where $R^1$ has the above-defined meaning), and then effect reaction of the compound of formula VI with an etherified hydroxylamine of formula $R^2O.NH_2$ ($R^2$ having the above define meaning) followed, if necessary, by removal of any carboxyl blocking or N-protecting groups. The reaction product may be separated to give the required syn isomer before or after removal of the said group or groups.

Where a starting material of formula V is employed, suitable carbamoylating agents include isocyanates of general formula

  (VIII)

where $R^{13}$ is a labile substituent group; such carbamoylating agents serve to form at the 3-position an N-protected carbamoyloxymethyl group of formula

(where $R^{13}$ has the above-defined meaning) which may be converted to the desired unsubstituted 3-carbamoyloxymethyl group by subsequent cleavage of the group $R^{13}$, for example by hydrolysis. Labile groups $R^{13}$ which are readily cleavable upon such subsequent treatment include chlorosulphonyl and bromosulphonyl; aralkyl groups such as benzyl, p-methoxybenzyl and diphenylmethyl; t-butyl; halogenated lower alkanoyl groups such as dichloroacetyl and trichloroacetyl; and halogenated lower alkoxycarbonyl groups such as 2,2,2-trichloroethoxycarbonyl. $R^{13}$ groups of this type, with the exception of aralkyl groups such as diphenylmethyl, may generally be cleaved by acid or base catalysed hydrolysis (e.g. by base catalysed hydrolysis using sodium bicarbonate). Halogenated groups such as chlorosulphonyl, trichloroacetyl and 2,2,2-trichloroethoxycarbonyl may also be cleaved reductively, while groups such as chloroacetyl may also be cleaved by treatment with thioamides such as thiourea. Aralkyl groups such as diphenylmethyl are conveniently cleaved by treatment with acid, e.g. a strong organic acid such as trifluoroacetic acid.

The carbamoylating agent of formula VIII is desirably used in excess (for example at least 1.1 moles relative to the compound of formula V). The carbamoylation may be assisted by the presence of base, e.g. a tertiary organic base such as a tri-(lower alkyl)amine (e.g. triethylamine) or by employing the acid V in the form of an alkali metal (e.g. sodium) salt, although such assistance may not be necessary in the case of more active isocyanates, e.g. compounds (VIII) when $R^{13}$ is a strongly electron-withdrawing group such as chlorosulphonyl or trichloroacetyl. Carbamoylations involving reaction of a free acid (V) with excess isocyanate (VIII) wherein $R^{13}$ is a group such as chlorosulphonyl or trichloroacetyl are thus of particular practical advantage by virtue of the simplicity of the reaction conditions, since there is no need for temporary blocking and subsequent deblocking of the 4-position carboxy group of the cephalosporin and since the electron withdrawing $R^{13}$ group in the resulting N-protected 3-carbamoyloxymethyl cephalosporin product is readily removed by, for example, hydrolysis with aqueous sodium bicarbonate.

It should be noted that it may be convenient to retain or even to introduce an N-substituting group $R^{13}$ during transformations of intermediate 3-carbamoyloxymethyl compounds in order to minimise unwanted side reactions involving the carbamoyloxymethyl group.

Another useful carbamoylating agent is cyanic acid, which is conveniently generated in situ from, for example, an alkali metal cyanate such as sodium cyanate, the reaction being facilitated by the presence of an acid, e.g. a strong organic acid such as trifluoroacetic acid. Cyanic acid effectively corresponds to the compound of formula VIII wherein $R^{13}$ is hydrogen and therefore converts compounds of formula V directly to their 3-carbamoyloxymethyl analogues.

3-Hydroxymethyl starting material for use in the process of this embodiment of the invention may be prepared by, for example, the methods described in British Pat. No. 1,121,308 and Belgian Pat. No. 783,449.

Any blocking group substituting the 4-carboxy group of compounds of formula III, V or VI is desirably a group which may readily be split off at a later stage of a reaction sequence and advantageously is a group containing 1-20 carbon atoms. Suitable blocked carboxyl groups are well known in the art, a list of representative groups being included in our aforementioned Belgian Pat. No. 783,449. Preferred blocked carboxyl groups include aryl lower alkoxycarbonyl groups such as p-methoxybenzyloxycarbonyl, p-nitrobenzyloxy carbonyl and diphenylmethoxycarbonyl; lower alkoxycarbonyl groups such as t-butoxycarbonyl; and lower haloalkoxycarbonyl groups such as 2,2,2-trichloroethoxycarbonyl. The carboxyl blocking group may subsequently be removed by any of the appropriate methods disclosed in the literature; thus, for example, acid or base catalysed hydrolysis is applicable in many cases, as are enzymically-catalysed hydrolyses.

Where at the end of a given preparative sequence a sulphoxide analogue of a compound of formula I is obtained, conversion to the corresponding sulphide may, for example, be effected by reduction of the corresponding acyloxysulphonium or alkyloxysulphonium salt prepared in situ by, for example, reaction with acetyl chloride in the case of an acetoxysulphonium salt, reduction being effected by, for example, sodium dithionite or by iodide ion (as in a solution of potassium iodide in a water miscible solvent such as acetic acid, tetrahydrofuran, dioxan, dimethylformamide or dimethylacetamide). The reaction may be effected at a temperature of $-20°$ to $+50°$ C.

Where the reaction product is a ceph-2-em-4-carboxylic ester the desired ceph-3-em compound may be obtained by treatment of the former with a base.

The antibiotic compounds according to the invention may be formulated for administration in any convenient way, by analogy with other antibiotics and the invention therefore includes within its scope a pharmaceutical composition comprising a compound of formula I or a non-toxic derivative (e.g. a salt, biologically acceptable ester, 1-oxide or solvate) thereof adapted for use in human or veterinary medicine. Such compositions may be presented for use in conventional manner with the aid of any necessary pharmaceutical carriers or excipients.

The antibiotic compounds according to the invention may be formulated for injection and may be presented in unit dose form in ampoules, or in multidose containers with added preservative. The compositions may take such forms as suspensions, solutions and emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

For veterinary medicine the compositions may, for example, be formulated as intramammary preparations in either long acting or quick-release bases.

In general the compositions may contain from 0.1% upwards, e.g. 0.1-99%, preferably from 10-60% of the active material, depending on the method of administration. Where the compositions comprise dosage units, each unit will preferably contain 50-1500 mg of the active ingredient. The dosage as employed for adult human treatment will preferably range from 500-4000 mg per day, depending on the route and frequency of administration.

The compounds according to the invention may be administered in combination with other compatible therapeutic agents such as antibiotics, for example penicillins, other cephalosporins or tetracyclines.

The following novel compounds, of value as intermediates in the preparation of antibiotic compounds of general formula I, comprise a further feature of the invention:

diphenylmethyl (6R,7R)-7-amino-3-trichloroacetylcarbamoyloxymethylceph-3-em-4-carboxylate and its toluene p-sulphonic acid salt;
diphenylmethyl (6R,7R)-7-amino-3-carbamoyloxymethylceph-3-em-4-carboxylate toluene p-sulphonic acid salt;
t-butyl (6R,7R)-7-[2-(fur-2-yl)-2-methoxyiminoacetamido]-3-hydroxymethylceph-3-em-4-carboxylate (syn isomer);
(6R,7R)-7-amino-3-chloroacetylcarbamoyloxymethylceph-3-em-4-carboxylic acid; and
(6R,7R)-7-amino-3-trichloroacetylcarbamoyloxymethylceph-3-em-4-carboxylic acid.

The following examples illustrate the invention. All temperatures are in °C. Melting points were determined on a Kofler block.

(A) PREPARATION OF STARTING MATERIALS

Preparation 1

(a) Diphenylmethyl (6R,7R)-7-(Thien-2-ylacetamido)-3-trichloroacetylcarbamoyloxymethylceph-3-em-4-carboxylate Trichloroacetyl isocyanate (13.2 g, 70 mmole) was added to a stirred suspension of diphenylmethyl (6R,7R)-3-hydroxymethyl-7-(thien-2-ylacetamido)-ceph-3-em-4 carboxylate (26.0 g, 50 mmole) in anhydrous acetone (600 ml) at 20°. The solid soon dissolved and after the mixture had been stirred at 20° for 1 hour it was chilled for 1 hour and the resulting solid was filtered off and washed with ether to give the title compound (33.1 g, 93%), m.p. 183° to 184°; $[\alpha]_D^{21} + 24°$ (c 0.95 in DMSO); $\lambda_{inf.}^{EtOH}$ 235 nm ($\epsilon$ 14,500) and $\lambda_{inf.}^{EtOH}$ 256 nm ($\epsilon$ 8,820).

IR, NMR and microanalytical data confirmed the structure as that of the title compound.

(b) Diphenylmethyl (6R,7R)-7-Amino-3-trichloroacetylcarbamoyloxymethylceph-3-em-4-carboxylate Toluene-p-sulphonic Acid Salt Anhydrous pyridine (31 ml, 0.384 mole) was added to a solution of phosphorus pentachloride (20 g, 96 mmole) in dry dichloromethane (300 ml) at 3°. The suspension was stirred for 10 minutes at 3° and diphenylmethyl (6R,7R)-7-(thien-2-ylacetamido)-3-trichloroacetylcarbamoyloxymethylceph-3-em-4-carboxylate (22.5 g, 32 mmole) was added; the reaction was stirred at ca. 2° for 1 hour. The dark solution was poured slowly into a cold (0°) anhydrous mixture of methanol (80 ml) and dichloromethane (200 ml) with the temperature kept below 5°. The temperature of the solution was then allowed to rise to 23° and, after stirring the solution at this temperature for 1 hour, water (200 ml) was added. The organic layer was separated and washed with 2N-sulphuric acid, water, sodium bicarbonate solution and water, dried over magnesium sulphate, and evaporated in vacuo. The resulting oil was dissolved in ethyl acetate and a solution of toluene-p-sulphonic acid monohydrate (6.0 g, 31.5 mmole) in ethyl acetate was added. The combined solutions (ca. 350 ml) were poured into diethyl ether (ca. 1 liter) and the resulting solid was filtered off and dried in vacuo to give the title compound (17.2 g, 72%), m.p. 150° to 153°; $[\alpha]_D^{21} + 7.5°$ (c 0.82 in DMSO); $\lambda_{max}^{EtOH}$ 263 nm ($\epsilon$ 7,600) and $\lambda_{inf.}^{EtOH}$ 267 nm ($\epsilon$ 7,350). IR, NMR and microanalytical data confirmed the structure as that of the title compound.

Evaporation of the filtrate and trituration of the residue with ethanol afforded unchanged starting material (3.2 g, 14.2%).

(c) Diphenylmethyl (6R,7R)-7-Amino-3-carbamoyloxymethylceph-3-em-4-carboxylate Toluene-p-sulphonic Acid Salt The toluene-p-sulphonic acid salt of diphenylmethyl (6R,7R)-7-amino-3-trichloroacetylcarbamoyloxymethylceph-3-em-4-carboxylate (17.2 g, 22.7 mmole) was dissolved in a mixture of anhydrous methanol (900 ml) and acetyl chloride (45 ml) and left to stand at 20° for 5 hours. Removal of the solvent under reduced pressure gave an oil, which was dissolved in dichloromethane. This solution was shaken with aqueous sodium bicarbonate solution and then washed with water. Toluene-p-sulphonic acid monohydrate (4.3 g, 22.7 mmole) was added and the solvent was evaporated in vacuo. The residue was dissolved in hot isopropanol (ca. 150 ml) and the solution was poured into diisopropyl ether (ca. 600 ml). The precipitated solid was filtered off and dried in vacuo to give the title compound (8.9 g, 64%), m.p. 110° to 112°; $[\alpha]_D^{21} - 14°$ (c, 1.0 in CHCl$_3$); $\lambda_{max}^{EtOH}$ 259 nm ($\epsilon$ 6,120) and $\lambda_{inf.}^{EtOH}$ 227 nm ($\epsilon$ 15,800).

IR, NMR and microanalytical data confirmed the structure as that of the title compound.

Preparation 2

Diphenylmethyl (6R,7R)-7-Amino-3-carbamoyloxymethylceph-3-em-4-carboxylate Toluene-p-sulphonic Acid Salt A stirred suspension of phosphorus pentachloride (156 g, 0.75 mole) in dry dichloromethane (1.5 liters) was cooled in an ice-bath and treated with pyridine (60.5 ml, 0.75 mole) at such a rate that the temperature of the mixture remained at ca. 20° to 25°. The mixture was stirred and cooled to 8° and diphenylmethyl (6R,7R)-7-(thien-2-yl)acetamido-3-trichloroacetylcarbamoyloxymethylceph-3-em-4-carboxylate (354.5 g, 0.5 mole) was added in portions over 10 minutes. The mixture was stirred at ca. 8° for 1.75 hours and then added over 10 minutes to a stirred mixture of butane-1,3-diol (225 ml, 2.5 mole) and dichloromethane (500 ml) precooled to $-20°$ so that the temperature of the mixture was kept in the range $-15°$ to $-20°$. The cooling bath was removed and the mixture was stirred at ca. $-10°$ for 20 minutes. Water (1 liter) was added and the two-phase mixture was stirred for 30 minutes. The aqueous phase was extracted with dichloromethane (2×500 ml), and the organic phases were washed sequentially with 2N hydrochloric acid (1 liter), combined and evaporated to a brown gum. The gum was dissolved in methanol (3.6 liters) and this solution was stirred and treated with saturated aqueous sodium hydrogen carbonate solution (1.2 liters) over a period of 10 minutes. The mixture was stirred at ca. 20° for 1.5 hours and a small quantity of brown solid was removed by filtration. The yellow filtrate was concentrated in vacuo (bath temp. not greater than 40°) to ca. 1.5 liters and water (1.5 liters) was added. The resulting suspension was refrigerated for 1 hour, and the yellow solid was filtered off, washed well with water, sucked as dry as possible and dried in vacuo at 40° for 24 hours. The greasy solid thus obtained, followed by toluene-p-sulphonic acid monohydrate (81 g, 0.425 mole), were added to stirred chloroform (2 liters). After several minutes the toluene-p-sulphonic acid salt began to crystallise. Stirring was continued for a further 30 minutes, after which the water was removed azeotropically in vacuo with continuous replacement of the chloroform so as to maintain a volume of 2 liters. The suspension was refrigerated overnight and the product was filtered off, slurry washed with chloroform (2×250 ml), refiltered, washed by displacement with chloroform (250 ml) and dried in vacuo at 40° to give the title compound as an off-white crystalline solid (237.8 g, 74.1%); $\lambda_{max}$(EtOH) 262 nm ($\epsilon$ 7,250); the NMR spectrum (Me$_2$SO-d$_6$) indicated the presence of 0.25 mole of chloroform.

Preparation 3

(6R,7R)-7-Amino-3-carbamoyloxymethylceph-3-em-4-carboxylic Acid

Diphenylmethyl (6R,7R)-7-amino-3-carbamoyloxymethylceph-3-em-4-carboxylate toluene-p-sulphonic acid salt (300.0 g, 0.44 mole), solvated with ca. 0.6 mole of chloroform, was added in portions over 30 minutes to a stirred mixture of trifluoroacetic acid (300 ml) and anisole (300 ml) immersed in a water-bath at 20°. The temperature of the mixture rose from 23° to 28° over the first 20 minutes but fell back to 26° by the end of the addition. The golden yellow solution was stirred for 1 hour, the temperature falling to 21°, and was then added to a stirred mixture of ethyl acetate (1.5 liters) and water (1.5 liters) immersed in an ice-bath. The pH of the stirred mixture was adjusted to 3.8 over 10 minutes with ammonia solution (S.G. 0.880), the temperature rising to 38°. The suspension was stirred and cooled to 10° over 1.25 hours and filtered. The cream solid was washed with water (750 ml) and ethyl acetate (4 × 200 ml) and dried in vacuo to give the title compound (115.6 g, 96.2%); $\lambda_{max}$ (pH6 phosphate) 265nm ($\epsilon$7,750); purity by HPLC (high pressure liquid chromatography) 99.7%.

Microanalytical data confirmed the structure as that of the title compound.

Preparation 4

(a)

(6R,7R)-7-(R-5-Benzoylamino-5-carboxypentanamido)-3-hydroxymethylceph-3-em-4-carboxylic Acid A stirred solution of (6R,7R)-7-(R-5-amino-5-carboxypentanamido)-3-hydroxymethylceph-3-em-4-carboxylic acid mono potassium salt (ca. 67% pure) (62.00g, ca. 100 mmole) in water (300 ml) was cooled to +5° and treated with a solution of benzoyl chloride (17.4 ml, 150 mmole) in acetone (200 ml) over 25 minutes. The pH of the reaction mixture was maintained at 8.2 to 8.5 by the controlled addition of 30% w/v aqueous tripotassium orthophosphate. The mixture was stirred for a further 10 minutes and was then covered with ethyl acetate (140 ml) and the pH was lowered to 5.6 with orthophosphoric acid. The layers were separated and the aqueous portion washed with more ethyl acetate (2×400 ml). The aqueous portion was diluted with water (2 liters), covered with ethyl acetate (2 liters), and the pH of the stirred mixture taken to 2.0 with orthophosphoric acid. The layers were separated and the aqueous layer extracted with further ethyl acetate (3×1500 ml). The combined extracts were washed with saturated brine (800 ml), dried, and concentrated in vacuo to a volume of 300 to 400 ml. The resulting slurry was stirred with ether (2 liters) for 20 minutes and was then filtered. The collected solid was washed with ether (2×250 ml) and dried in vacuo (1 mm.) to give the title compound as a white solid (54.95 g, 88.6% w/w), $[\alpha]_D^{20}$ + 74° (c 1.00, dioxan); $\lambda_{max}$(pH 6 buffer) 231nm (E$_{1cm}^{1\%}$ 275), 266nm (inflexion, E$_{1cm}^{1\%}$ 145). The NMR spectrum (Me$_2$SO-d$_6$) showed the presence of ca. 20% lactone impurity and ethyl acetate (ca. 0.4 mole).

(b)

(6R,7R)-7-(R-5-Benzoylamino-5-carboxypentanamido)-3-chloroacetylcarbamoyloxymethylceph-3-em-4-carboxylic Acid Monosodium Salt The product of (a) above (25.46 g) was treated with a solution of chloroacetylisocyanate (9.00 g, 75 mmole) in dry acetone (92 ml). The resulting solution was stirred for 25 minutes at ca. 20°, then cooled to ca. 5° over 5 minutes and treated with a solution of sodium 2-ethylhexanoate (8.47 g, 51 mmole) in acetone (51 ml). The crystalline suspension was stirred at ca. 5° for 5 minutes, and the solid was collected by filtration, washed with acetone (80 ml) and ether (250 ml), then dried in vacuo (1 mm.) to give the title compound (27.23 g, 107.0% w/w), $[\alpha]_D^{20}$ + 72.0° (c 1.00, 3% aqueous NaHCO$_3$); $\lambda_{max}$(pH6 buffer) 227nm (E$_{1cm}^{1\%}$ 249), 261nm (inflexion, E$_{1cm}^{1\%}$ 105). The NMR spectrum (Me$_2$SO-d$_6$) showed the presence of ca. 35% lactone impurity and chloroacetamide (ca. 1.0 mole).

(c)

(6R,7R)-7-Amino-3-chloroacetylcarbamoyloxymethylceph-3-em-4-carboxylic Acid

A suspension of the product of (b) above (24.77 g) in dry methylene chloride (320 ml) under nitrogen was cooled to ca. 10° with stirring. Pyridine (17.60 ml, 218.0 mmole), then dichlorodimethylsilane (16.80 ml, 139.2 mmole) were added and the pale-brown suspension was stirred at ca. 20° for 20 minutes and was then cooled to −17°. Phosphorous pentachloride (10.84 g, 52.0 mmole) was added and the mixture was stirred at −17° to −23° for 2 hours. Pyridine (6.48 ml, 80.4 mmole) was added, and the mixture was added to methanol (104 ml + 20 ml washings, pre-cooled to −35°) at such a rate that the temperature of the stirred solution did not exceed −10°. The stirred solution was allowed to reach +2° over 25 minutes, then water (88 ml) was added, and the pH of the mixture was taken from 0.6 to 3.8 with aqueous ammonia solution (S.G. 0.880). The resulting two-phase mixture containing a precipitated solid was refrigerated for 1 hour and was then filtered. The solid was successively washed with 50% v/v aqueous methanol (100 ml), methanol (80 ml), and methylene chloride (40 ml), then dried in vacuo (1 mm.) to give the title compound as a cream powder (6.86 g, 27.7%, w/w), $[\alpha]_D^{19}$ + 48° (c 1.04, Me$_2$SO); $\lambda_{max}$(pH 6 buffer) 237.5nm (E$_{1cm}^{1\%}$ 149), 261.5nm (E$_{1cm}^{1\%}$ 145).

(B) EXAMPLES

Example 1

(a) Diphenylmethyl (6R,7R)-3-Carbamoyloxymethyl-7-[2-(fur-2-yl)-2-methoxyiminoacetamido]ceph-3-em-4-carboxylate (syn isomer)

Method (i)

Crude diphenylmethyl (6R,7R)-7-amino-3-carbamoyloxymethylceph-3-em-4-carboxylate toluene-p-sulphonic acid salt obtained from the corresponding 3-trichloroacetylcarbamoyloxymethyl compound (25.0 g, 0.33 mole) was dissolved in a mixture of ethyl acetate and aqueous sodium bicarbonate solution. The organic layer was separated, washed with water, dried over magnesium sulphate, and evaporated on a rotary evaporator to give diphenylmethyl (6R,7R)-7-amino-3-carbamoyloxymethylceph-3-em-4-carboxylate (11.5 g, 0.262 mole, 77%) as a foam.

2-(Fur-2-yl)-2-methoxyiminoacetic acid (syn isomer) (5.32 g, 0.312 mole) in dry dichloromethane (100 ml) was added to a solution of this amine in dichloromethane (50 ml) cooled to 3°, followed 10 minutes later by a solution of DL-dicyclohexylcarbodiimide (6.5 g, 0.312 mole) in dichloromethane (30 ml). The reaction mixture was stirred in an ice-bath for 45 minutes during which time a solid (presumably N,N'-dicyclohexyl urea) crystallised out. This was filtered off and discarded, and the filtrate was washed with aqueous sodium bicarbonate solution and water, dried over mangesium sulphate, and evaporated to dryness. The residue was triturated with ethanol to give a crude product (10.6 g) which was purified by chromatography on Silica Gel (1kg). Elution with 10% acetone in dichloromethane removed non-polar impurities, and fractions eluted with 20% acetone in dichloromethane gave the title compound (4.8 g, 31%), m.p. 199° to 202°; $[\alpha]_D^{21°}$ + 14° (c, 1.0 in DMSO); $\lambda_{max}^{EtOH}$ 277 nm ($\epsilon$ 18,600) and $\lambda_{inf}^{EtOH}$ 270 nm ($\epsilon$ 17,900).

IR, NMR and microanalytical data confirmed the structure as that of the title compound.

Method (ii)

Triethylamine (1.86 g, 18.4 mmole) was added to a dichloromethane solution (35 ml) of 2-(fur-2-yl)-2-methoxyiminoacetic acid (syn isomer) (3.1 g, 18.4 mmole). After cooling this solution in an ice-bath for 5 minutes, oxalyl chloride (1.57 ml. 18.4 mmole) and a drop of N,N-dimethylformamide were added. After 0.5 hours the solvent was removed under reduced pressure and the solid residue was dried for 1 hour in vacuo. Anhydrous ether (150 ml) was added to dissolve the acid chloride that had been formed and the insoluble triethylamine hydrochloride (2.5 g) was filtered off. The ether was evaporated on a rotary evaporator and the oily residue was redissolved in dichloromethane.

Diphenylmethyl (6R,7R)-7-amino-3-carbamoyloxymethylceph-3-em-4-carboxylate toluene-p-sulphonic acid salt (8.9 g, 14.7 mmole) was dissolved in anhydrous dichloromethane. This solution was shaken with aqueous sodium bicarbonate solution, washed with water, and dried over magnesium sulphate. To this solution of the free amine were added the dichloromethane solution of 2-(fur-2-yl)-2-methoxyiminoacetyl chloride (syn isomer) and propylene oxide (5 ml). After 10 minutes a crystalline solid (1.1 g) was filtered off, which was subsequently identified as diphenylmethyl (6R,7R)-7-amino-3-carbamoyloxymethylceph-3-em-4-carboxylate hydrochloric acid salt. The filtrate was washed with 2N-sulphuric acid, water, aqueous sodium bicarbonate solution and water, and was dried over magnesium sulphate and evaporated to dryness to yeild the title compound (2.5 g, 30.5%), similar in physical properties to the product of Method (i) above.

(b) Sodium (6R,7R)-3-Carbamoyloxymethyl-7-[2-(fur-2-yl)-2-methoxyiminoacetamido]ceph-3-em-4-carboxylate (syn isomer)

Trifluoroacetic acid (20 ml) was added slowly to a mixture of anisole (5 ml) and diphenylmethyl (6R,7R)-3-carbamoyloxymethyl-7-[2-(fur-2-yl)-2-methoxyiminoacetamido]ceph-3-em-4-carboxylate (syn isomer) (4.7 g, 8 mmole) which had been cooled in an ice-bath. The flask was shaken occasionally during the next 10 minutes to ensure complete solution of the solid. It was then removed from the ice-bath and excess trifluoroacetic acid was removed on a rotary evaporator. Trituration of the residue with ethyl acetate (5 ml) gave (6R,7R)-3-carbamoyloxymethyl-7-[2-(fur-2-yl)-2-methoxyiminoacetamido]ceph-3-em-4-carboxylic acid (syn isomer) (3.3 g, 94%) as a solid which was filtered off and washed with diethyl ether.

The free acid was dissolved in acetone and a slight excess of sodium 2-ethylhexanoate in acetone (8.0 ml of a molar solution) was added. After the reaction mixture had been stirred at 0° for 2 hours, the title salt (2.3 g, 73%) was filtered off. This was combined with another batch of the title salt (0.8 g) and purified by washing an aqueous solution (250 ml) with ether (2×100 ml, 1×50 ml). The aqueous solution was freeze-dried to give sodium (6R,7R)-3-carbamoyloxymethyl-7-[2-(fur-2-yl)-2-methoxyiminoacetamido]ceph-3-em-4-carboxylate (syn isomer) (2.66 g), $[\alpha]_D^{21}$ +73.5° (c 1.06 in Me$_2$SO); $\lambda_{max}^{pH\ 6}$ 274 nm ($\epsilon$ 16,500); $\nu_{max}$ (Nujol) 3450, 3330, 3250, (NH,NH$_2$ and H$_2$O), 1752 (azetidin-2-one) and 1652 and 1600 cm$^{-1}$ (carboxylate); $\tau$(Me$_2$SO-d$_6$) 0.24 (d,J8Hz, CONH), 2.12 (d, J2Hz, furyl C$_5$-H), 3.25 and 3.30 (m, furyl C$_3$-H and C$_4$-H), 3.44 (broad s, CONH$_2$), 4.34 (dd, J 5 and 8Hz, C$_7$-H), 4.92 (d, J4.5Hz, C$_6$-H), 5.15 (q, J13Hz C$_3$-CH$_2$), 6.07 (s, NOCH$_3$) and 6.58 (q, J 18Hz, C$_2$-H$_2$)

(Found: C,42.0; H,3.8; N,12.1; S,7.2. C$_{16}$H$_{15}$N$_4$NaO$_8$S.O.5H$_2$O(455.37) requires C,42.2; H,3.5; N,12.3 and S,7.0%).

Example 2

(6R,7R)-3-Carbamoyloxymethyl-7-[2-(fur-2-yl)-2-methoxyiminoacetamido]ceph-3-em-4-carboxylic Acid (syn isomer)

A stirred mixture of N,N-dimethylacetamide (75 ml), acetonitrile (75 ml), triethylamine (42 ml, 0.3 mole) and (6R,7R)-7-amino-3-carbamoyloxymethylceph-3-em-4-carboxylic acid was immersed in an ice-bath and water (10 ml) was added. The mixture was stirred at 0° to 2° for 45 minutes, the solid slowly dissolving to give a yellow solution.

Meanwhile a stirred suspension of phosphorus pentachloride (14.99 g, 0.072 mole) in dry dichloromethane (150 ml) was cooled to 0°, and N,N-dimethylacetamide (27.5 ml) was added. The resulting solution was re-cooled to −10° and 2-(fur-2-yl)-2-methoxyiminoacetic acid (syn isomer) (12.17 g, 0.072 mole) was added. The mixture was stirred at −10° for 15 minutes and crushed ice (35 g) was added. The mixture was stirred at 0° for 10 minutes, whereafter the lower dichloromethane phase was added over 10 minutes to the cephalosporin solution prepared above, cooled to −10° so that the reaction temperature rose steadily to 0°. The mixture was stirred at 0° to 2° for 1 hour, whereafter the cooling bath was removed and the reaction temperature allowed to rise to 20° over 1 hour. The reaction mixture was then added slowly to 2N hydrochloric acid (100 ml) diluted with cold water (1.15 liters) at 5°. The pH of the two-phase mixture was adjusted to below 2 with 2N hydrochloric acid (10 ml), and the mixture was stirred and recooled to 5°. The solid which precipitated was filtered, washed with dichloromethane (100 ml) and water (250 ml), and dried in vacuo at 40° overnight to give the title compound (22.04 g, 86.6%), $[\alpha]_D^{20}$ + 58° (c 1.08, Me$_2$SO); $\lambda_{max}$ (pH 6 phosphate buffer) 274 nm ($\epsilon$ 17,500); $\nu_{max}$ (Nujol) 3480, 3440, 3367, 3255 and 3133 (bonded NH and NH$_2$), 2725 and 2590 (CO$_2$H), 1760 (azetidin-2-one), 1728, 1712 and 1698 (OCONH$_2$ and CO$_2$H), 1655 and 1530 cm$^{-1}$ (CONH); $\tau$(Me$_2$SO-d$_6$) 0.25 (d, J 8 Hz; CON$\underline{H}$), 2.18 (s, furyl C$_5$-$\underline{H}$), 3.28 and 3.4 (m, furyl C$_4$-$\underline{H}$ and C$_3$-$\underline{H}$), 3.42 (s, CON$\underline{H}_2$), 4.19 (dd, J 8 and 5 Hz; C$_7$-$\underline{H}$), 4.80 (d, J 5 Hz; C$_6$-H), 5.06 and 5.39 (q, J 13 Hz; C$_3$-$\underline{CH}_2$), 6.09 (g; NO$\underline{CH}_3$), 6.44 collapsed q; C$_2$-$\underline{H}_2$), and 7.99 (0.03 mole C$\underline{H}_3$CON(CH$_3$)$_2$).

Example 3

(a)

(6R,7R)-7-(R-5-Benzoylamino-5-carboxypentanamido)-3-hydroxymethylceph-3-em-4-carboxylic Acid Monoquinolinium Salt Monohydrate A stirred solution of (6R,7R)-7-(R-5-amino-5-carboxypentanamido)-3-hydroxymethylceph-3-em-4-carboxylic acid, monopotassium salt (18.45 g, 30 mmole) in water (93 ml) was cooled to 0° to 5° (ice/water bath) and treated with a solution of benzoyl chloride (5.19 ml, 45 mmole) in acetone (63 ml) over 25 minutes. The pH of the reaction mixture was maintained at pH 8.5 ($\pm$0.1) by the controlled addition of 30% w/v aqueous tripotassium orthophosphate (ca. 100 ml). The mixture was stirred for a further 5 minutes, covered with ethyl acetate (150 ml) and the pH was then lowered to 5.6 with orthophosphoric acid. The layers were separated and the aqueous portion washed with additional ethyl acetate (2 $\times$ 300 ml). The combined washings were extracted with water (200 ml). The combined aqueous portion and washings were diluted with water (600 ml), covered with ethyl acetate (600 ml), and the pH of the stirred mixture was taken to 2.0 with orthophosphoric acid. The organic layer was separated and quinoline (10.64 ml, 45 mmoles) in ethyl acetate (25 ml) was added, with stirring, to give a white precipitate. The aqueous portion was extracted with further ethyl acetate (3 $\times$ 300 ml) and these were added to the suspension containing quinoline. The mixture was stirred for 1 hour at ca. 18° and then concentrated in vacuo to ca. 500 ml. Ether (900 ml) was added with stirring and after 30 minutes the solid was collected by filtration, washed with ether (5 $\times$ 200 ml) and dried in vacuo (1 mm) to give the title compound as a white powder (19.20 g, 104.1% w/w), $[\alpha]_D^{18}$ + 78° (c 1.00, dioxan); $\lambda_{max}$ (pH 6 buffer) 258 nm (inflection, $E_{1cm}^{1\%}$ 185). IR and NMR data confirmed the structure as that of the title compound containing ca. 15% lactone impurity and trace amounts of ether and ethyl acetate.

(b)

(6R,7R)-7-(R-5-Benxoylamino-5-carboxypentanamido)-3-trichloroacetylcarbamoyloxymethylceph-3-em-4-carboxylic Acid Monoquinolinium Salt The product of (a) above (4.24 g, equivalent to 7 mmole) was treated with dry dioxan (100 ml) in which it partially dissolved. To the stirred mixture was added trichloroacetylisocyanate (2.90 ml, 24.5 mmoles). The resulting solution was stirred for 30 minutes, and was then clarified by filtration and evaporated in vacuo to give a yellow foam. This was dissolved in acetone (ca. 10 ml) and poured into stirred isopropyl ether (ca. 100 ml). The resulting white precipitate was collected by filtration and dried in vacuo (1 mm) to give the title compound as a white powder (6.26 g, 147.8% w/w). NMR data confirmed the structure as that of the title compound and also showed the presence of lactone (ca. 22%), isopropyl ether (0.75 mole), dioxan (0.2 mole) and a small amount of acetone.

(c)

(6R,7R)-7-Amino-3-trichloroacetylcarbamoyloxymethylceph-3-em-4-carboxylic Acid

A solution of the product of (b) above (4.77 g, equivalent to 6 mmoles) in dry methylene chloride (40 ml) under nitrogen was cooled to ca. 10° with stirring. Pyridine (2.20 ml, 27.3 mmoles) then dichlorodimethylsilane (2.10 ml, 17.4 mmoles) were added and the brown solution was stirred at ca. 17° for 20 minutes and then cooled to $-17°$. Phosphorus pentachloride (1.355 g, 6.5 mmoles) was added and the mixture was stirred at ca. $-16°$ for 2 hours. Pyridine (0.81 ml, 10 mmoles) was added and the mixture was added to methanol (13 ml + 2.5 ml washings, pre-cooled to $-35°$) at such a rate that the temperature of the stirred solution did not exceed $-10°$. The stirred solution was allowed to reach +9° over 25 minutes, water (11 ml) was then added and the pH of the mixture was taken from 0.3 to 3.8 with ammonia solution (S.G. 0.880). The resulting two-phase mixture containing a precipitated solid was refrigerated for 1 hour and then filtered. The solid was successively washed with 50% v/v aqueous methanol (12 ml), methanol (10 ml) and methylene chloride, (5 ml) then dried in vacuo (1 mm) to give the title compound as a cream powder (1.22 g, 25.6% w/w), $[\alpha]_D$ +44° (c 1.02, Me$_2$SO); $\lambda_{max}$ (pH 6 buffer) 240 nm ($E_{1cm}^{1\%}$ 133), 263 nm ($E_{1cm}^{1\%}$ 140). NMR data confirmed the structure as that of the title compound.

(d)

(6R,7R)-3-Carbamoyloxymethyl-7-[2-(fur-2-yl)-2-methoxyiminoacetamido]ceph-3-em-4-carboxylic Acid (syn isomer)

Phosphorus pentachloride (4.5 g, 21.5 mmoles) was dissolved in dry methylene chloride (90 ml) and cooled with stirring to $-15°$. N,N-Dimethylacetamide (9 ml) was added slowly, keeping the temperature below $-10°$, and the mixture was stirred for 10 minutes. 2-(Fur-2-yl)-2-methoxyiminoacetic acid (syn isomer) (3.66 g, 21.5 mmoles) was added and the mixture stirred at $-15°$ for 15 minutes. Crushed ice (18 g) was added carefully so that the temperature of the mixture did not exceed $-7°$. The mixture was stirred for 10 minutes and the organic portion was separated and added dropwise to a solution of (6R,7R)-7-amino-3-trichloroacetylcarbamoyloxymethylceph-3-em-4-carboxylic acid (7.52 g, 18 mmoles) in dry methylene chloride (90 ml) and triethylamine (5.5 ml, 40 mmoles), precooled to $-10°$. The acid chloride solution was added over 20 minutes, the temperature of the reaction mixture being maintained between $-10°$ and $-8°$. The mixture was then stirred for 80 minutes, during which time the temperature was allowed to rise to +3°, and methanol (6 ml) was added. After a further 5 minutes stirring, the solution was extracted with 3% w/v aqueous sodium hydrogen carbonate (2 $\times$ 120 ml) and water (150 ml). The combined extracts were left to stand at ca. 20° for 3.5 hours, and were then washed with ethyl acetate (100 ml) and acidified to pH 1.5 with concentrated hydrochloric acid. The resulting deposited oil was extracted into ethyl acetate (2 $\times$ 300 ml). The combined organic portions were washed with water (2 $\times$ 100 ml), dried (MgSO$_4$) and evaporated in vacuo to give a yellow solid (7.1 g) which was stirred with ether (150 ml), filtered, and dried in vacuo (1 mm) to give the title compound as a pale yellow solid (5.20 g, 68.2% of theory), $\lambda_{max}$ (pH 6 buffer) 275 nm ($E_{1\ cm}^{1\%}$ 385). IR and NMR data confirmed the structure as that of the title compound containing a trace of ether.

Example 4

(6R,7R)-3-Carbamoyloxymethyl-7-[2-methoxyimino-2-(thien-2-yl)acetamido]ceph-3-em-4-carboxylic Acid (syn isomer)

Following the procedure of Example 2, the title compound (888 mg., 50%) was prepared from (6R,7R)-7-amino-3-carbamoyloxymethylceph-3-em-4-carboxylic acid (1.09 g., 4 mmole) and sodium 2-methoxyimino-2-(thien-2-yl)acetate (syn -isomer) (923mg., 4.8 mmole). Its properties are: m.p. 157° to 163°, $[\alpha]_D^{20} + 57.3°$ (c 1.0 in dioxan), $R_{PAC}$ 0.8* Solvent system A*, $\lambda_{max}$ (pH6 buffer) 262.5 nm ($\epsilon$ 15,550), and inflexion at 235 nm ($\epsilon$ 10,350), $\tau$ (DMSO-$d_6$) 0.20 (d, J 8 Hz, NH), 2.29 (dd, J 2 and 5 Hz, thienyl $C_5$-H), 2.7 to 2.9 (m, thienyl $C_3$-H and $C_4$-H), 3.40 (s, $CONH_2$), 4.13 (dd, J 5 and 8 Hz, $C_7$-H), 4.75 (d, J 5 Hz, $C_6$-H), 5.01 and 5.34 (AB-q, J 13 Hz, $C_3$-$CH_2$), 6.08 (s, $NOCH_3$), and 6.42 (collapsed AB-q, $C_2$-$H_2$), $\nu_{max}$ (Nujol) 3700 to 2100 ($CO_2H$), 3480, 3440, 3365, and 3255 (NH and $NH_2$), 1760 (azetidin-2-one), 1722 ($CO_2H$), 1709 ($OCONH_2$) and 1652 and 1530 cm$^{-1}$ (amide).

*See "Notes" after Table 1

Example 5

(6R,7R)-3-Carbamoyloxymethyl-7-[2-(fur-2-yl)-2-methoxyiminoacetamido]ceph-3-em-4-carboxylic Acid (syn isomer)

N,N-Dimethylacetamide (1.5 ml) was added to a solution of phosphorus pentachloride (750 mg, 3.6 mmole) in anhydrous dichloromethane (15 ml) cooled to −10°. After 10 minutes, 2-(fur-2-yl)-2-methoxyiminoacetic acid (syn isomer) (612 mg, 3.6 mmole) was added to the resulting suspension, which soon became a clear solution and was stirred at −10° for 15 minutes. Ice (3 g) was added and after 10 minutes the layers were allowed to separate in a dropping funnel. The organic phase was slowly (over 5 minutes) run into a cooled (−10°) solution of (6R,7R)-7-amino-3-chloroacetylcarbamoyloxymethylceph-3-em-4-carboxylic acid (1.05 g, 3 mmole) in dichloromethane (15 ml) containing triethylamine (0.9 ml, 6.5 mmole). Methanol (1 ml) was added after 40 minutes, and 5 minutes later the reaction mixture was extracted twice with 3% w/v aqueous sodium bicarbonate solution (150 ml). The aqueous extract was washed with ethyl acetate (25 ml) and left at 20° for 4 hours. The solution was washed twice with ethyl acetate, acidified with 2N-hydrochloric acid, and extracted 3 times with ethyl acetate. The combined organic layers were dried over magnesium sulphate, decolourised with activated charcoal, and evaporated in vacuo to give a pale-yellow solid (1.15 g, 87%). This was washed with diethyl ether and filtered off to give the title compound (0.91 g, 71%); $\lambda_{max}^{pH6}$ 274 nm ($\epsilon$ 17,300). The IR and NMR spectra of the product agreed with those of an authentic sample.

Example 6

(6R,7R)-3-Carbamoyloxymethyl-7-[2-(fur-2-yl)-2-methoxyiminoacetamido]ceph-3-em-4-carboxylic Acid (syn isomer Method (i)

Acetone (750 ml) was cooled to 0° and treated with trichloroacetyl isocyanate (28.8 ml, 240 mmole), and the solution was recooled to 0°. (6R,7R)-7-[2-(fur-2-yl)-2-methoxyiminoacetamido]-3-hydroxymethylceph-3-em-4-carboxylic acid (syn isomer) (45.6 g, 120 mmole) was added to the stirred isocyanate solution in portions over 5 minutes so that the reaction temperature did not exceed 6°. The yellow solution was stirred for a further 15 minutes and methanol (4.5 ml) was added. The solution was concentrated to 60 ml and the concentrate dissolved in methanol (750 ml). Sodium bicarbonate (45.3 g, 540 mmole) in water (600 ml) was added, followed by activated charcoal (4.5 g), and the resulting suspension was stirred at room temperature for 2 hours. The charcoal was removed by filtration through Keiselguhr and the light yellow filtrate was adjusted to pH 4.5 by the addition of dilute hydrochloric acid. The solution was concentrated to half volume under reduced pressure and an equal volume of water was added. The pH was adjusted to 2.0 with dilute hydrochloric acid and the product was isolated by filtration, washed with water (3 × 150 ml) and dried at 40° for 16 hours in vacuo to give the title compound (37.46 g, 73.5%); $[\alpha]_D^{20} + 63.7°$ (c 1.0; 0.2 M pH 7 phosphate buffer); $\lambda_{max}$ (pH6 phosphate buffer) 274 nm ($\epsilon$ 17,600).

IR, NMR and microanalytical data confirmed the structure as that of the title compound.

Method (ii)

A slurry of (6R,7R)-7-[2-(fur-2-yl)-2-methoxyiminoacetamido]-3-hydroxymethylceph-3-em-4-carboxylic acid (syn isomer) (3.81 g, 9.55 mmole) in dichloromethane (70 ml)/tetrahydrofuran (25 ml) at 5° was treated with dichloroacetyl isocyanate (2.6 ml, 25 mmole). The reaction mixture was then treated in the same manner as in Method (i) to give the title compound (3.36 g, 83.0%); $[\alpha]_D^{20} + 63°$; $\lambda_{max}$ 273.5 nm ($\epsilon$ 17,800); with similar IR and NMR spectra to the product of Method (i).

Method (iii)

A slurry of (6R,7R)-7-[2-(fur-2-yl)-2-methoxyiminoacetamido]-3-hydroxymethylceph-3-em-4-carboxylic acid (syn isomer) (19.05 g, 50 mmole) in dry acetonitrile (250 ml) was treated at between 5 and 10° with chlorosulphonyl isocyanate (6.33 ml, 75 mmole) in acetonitrile (80 ml). The reaction was stirred at between 0° and 5° for 10 minutes and water (50 ml) was added. The mixture was stirred at ca 20°, and after 20 minutes a white crystalline solid separated. Evaporation and filtration gave the title compound (18.17 g, 85.7%); $[\alpha]_D^{20} + 62.5°$; $\lambda_{max}$ 273.5 nm ($\epsilon$ 17,820); with similar IR and NMR spectra to the product of Method (i). A second crop (1.88 g, 8.6%) of the product, with similar constants, was obtained by evaporation of the mother liquors.

Example 7

Form I Sodium (6R,7R)-3-Carbamoyloxymethyl-7-[2-(fur-2-yl)-2-methoxyiminoacetamido]ceph-3-em-4-carboylate (syn isomer)

Method (i)

(6R,7R)-3-Carbamoyloxymethyl-7-[2-(fur-2-yl)-2-methoxyiminoacetamido]ceph-3-em-4-carboxylic acid (syn isomer) (100 g) in N,N-dimethylacetamide (400 ml)/acetone (1 liter) was treated with sodium 2-ethylhexanoate (40 g) in acetone (200 ml). The mixture was seeded and stirred at ambient temperature for 1.25 hours. The product was filtered off, washed with acetone (500 ml) and then slurried with acetone (3×300 ml) and finally slurried with ether to give the title compound (101.4 g, 92.5%) containing (after equilibration in the atmosphere) 0.65 mole equivalents of water. The product has $[\alpha]_D + 61°$ (c 0.5, pH 4.5 phosphate buffer) and $\lambda_{max}$ 273 nm $E_{1cm}^{1\%}$ 412 ($H_2O$).

IR and NMR data confirmed the structue as that of the title compound, the IR spectrum indicating that the compound was the Form I salt.

Method (ii)

The process of Method (i) was repeated, except that the cephalosporin acid was initially dissolved in N,N-dimethylformamide/industrial methylated spirits in place of N,N-dimethylacetamide/acetone, to yield the title compound (80%) similar in properties to the product of Method (i). The IR spectrum indicated that the compound was the Form I salt.

Method (iii)

(6R,7R)-3-Carbamoyloxymethyl-7-[2-(fur-2-yl)-2-methoxyiminoacetamido]ceph-3-em-4-carboxylic acid (syn isomer) (4.24 g, 10 mmoles) was dissolved in N,N-dimethylacetamide (20 ml) which had been dried over molecular sieve (Linde 4A) for 24 hours. To this was added a solution of sodium 2-ethylhexanoate (2.0 g, 12 mmoles recrystallised from dioxan and dried over phosphorus pentoxide) in ethyl acetate (80 ml) which had been dried over molecular sieve (Linde 4A) for 24 hours. The solution was stirred in a closed vessel for about 15 minutes until crystallisation commenced and then cooled to 4° for one hour. The product was filtered, washed with dry ethyl acetate (~ 100 ml) and, while still wet with this solvent, was transferred to an oven and dried at 20° in vacuo over phosphorus pentoxide overnight to afford the title compound (3.89 g, 87%).

The IR and NMR spectra of the product conformed to those of an authentic sample.

Example 8

Form II Sodium (6R,7R)-3-Carbamoyloxymethyl-7-[2-(fur-2-yl)-2-methoxyiminoacetamido]ceph-3-em-4-carboxylate (syn isomer)

Method (i)

Charcoal (0.2 g) was added to a solution of (6R,7R)-3-carbamoyloxymethyl-7-[2-(fur-2-yl)-2-methoxyiminoacetamido]ceph-3-em-4-carboxylic acid (syn isomer) (4.00 g, 9.42 mmole) in a mixture of acetone (132 ml) and water (1.33 ml). The suspension was stirred for 30 minutes and filtered through a bed of Kieselguhr, the filter bed being washed with acetone (10 ml). A filtered solution of sodium 2-ethylhexanoate (1.66 g, 10 mmole) in acetone (20 ml) was added over 1 hour to the stirred filtrate. The resulting suspension was stirred for a further 10 minutes, and the white solid was filtered off, washed with acetone (2 × 25 ml) and dried in vacuo to give the title compound (4.06 g, 93.0%); $[\alpha]_D^{20} + 60°$ (c 0.91, $H_2O$); $\lambda_{max}(H_2O)$ 274 nm ($\epsilon$ 17,400); (Found: C, 41.0, 41.2; H, 3.45, 3.6; N, 12.3, 12.4; Na, 5.2; S, 6.6, 6.85; $H_2O$, 2.7, 2.7. $C_{16}H_{15}N_4NaO_8S$. 0.7 $H_2O$ (459.0) requires C, 41.8; H, 3.6; N, 12.2; Na, 5.0; S, 7.0; $H_2O$, 2.7%); purity by HPLC 99.4%. The NMR spectrum of the product resembled that of an authentic sample, and the IR spectrum indicated that the product was the Form II salt.

Method (ii)

(6R,7R)-3-Carbamoyloxymethyl-7-[2-(fur-2-yl)-2-methoxyiminoacetamido]ceph-3-em-4-carboxylic acid (syn isomer) (16.98 g, 40 mmoles) was added to a stirred mixture of acetone (333 ml) and water (8.5 ml). After treatment with charcoal and filtration of this solution, sodium 2-ethylhexanoate (7.32 g, 44 mmoles) in acetone (85 ml) was added slowly over 1 hour. The reaction mixture was stirred for 15 minutes, filtered, and the product was washed with acetone (2 × 65 ml) and dried in vacuo at 20° overnight to yield the title compound (17.95 g, 98.5%), containing 0.5 mole $H_2O$. The NMR spectrum of the product conformed to that of an authentic sample, and the IR spectrum indicated that the product was the Form II salt.

Example 9

Form III Sodium (6R,7R)-3-Carbamoyloxymethyl-7-[2-(fur-2-yl)-2-methoxyiminoacetamido]ceph-3-em-4-carboxylate (syn isomer)

Sodium (6R,7R)-3-carbamoyloxymethyl-7-[2-(fur-2-yl)-2-methoxyiminoacetamido]ceph-3-em-4-carboylate (syn isomer) (4.0 g) was dissolved in water (20 ml). Industrial methylated spirits (20 ml) and dioxan (160 ml) were added and the solution was filtered and then set aside at 4° to crystallise. The very white needle-shaped crystals were filtered off, washed with dioxan (100 ml) and, while still wet with dioxan, were transferred to an oven and dried at 20° in vacuo overnight to yield the title compound (3.96 g, 78.5%). The IR and NMR spectra of the product conformed to those of an authentic sample.

Example 10

Form IV Sodium (6R,7R)-3-Carbamoyloxymethyl-7-[2-(fur-2-yl)-2-methoxyiminoacetamido]ceph-3-em-4-carboxylate (syn isomer)

Sample of Form I and Form III sodium 3-carbamoyloxymethyl-7-[2-(fur-2-yl)-2-methoxyiminoacetamido]ceph-3-em-4-carboxylate (syn isomer), prepared according to Method (iii) of Example 7 and Example 9 respectively, were exposed to moisture (75% relative humidity) for 3 days to give the title compound. The IR and NMR spectra of the products conformed to those of an authentic sample. Karl-Fischer water analysis gave, respectively, 4.0 and 3.85% (1 mole $H_2O$ is equivalent to 3.9%).

Example 11

(a) t-Butyl (6R,7R)-3-Carbamoyloxymethyl-7-[2-(fur-2-yl-2-methoxyiminoacetamido]ceph-3-em-4-carboxylate (syn isomer)

A suspension of (6R,7R)-3-carbamoyloxymethyl-7-[2-(fur-2-yl)-2-methoxyiminoacetamido]ceph-3-em-4-carboxylic acid (syn isomer) (4.4 g) in dry methylene chloride (200 ml) was treated with O-t-butyl-N,N'-dicyclohexylisourea (6.6 ml), whereby a pale-yellow solution was formed. After 24 hours at 23°, starting material remained and more isourea (3.3 ml) was added. After 48 hours, the mixture was filtered and the filtrate evaporated under reduced pressure. The resulting material was slurried with ether/ethyl acetate to remove remaining dicyclohexylurea. The filtrate was washed with saturated aqueous sodium hydrogen carbonate and water, then was dried and evaporated to give a foam (5.2 g). Chromatography on silica gel with toluene:ethyl acetate = 2:1 as solvent gave the title compound (3.9 g) as a pale-yellow foam, $\lambda_{max}$(ethanol) 275.5 nm ($\epsilon$ 18,400).

IR and NMR data confirmed the structure as that of the title compound.

(b) t-Butyl (1R,6R,7R)-3-Carbamoyloxymethyl-7-[2-(fur-2-yl)-2-methoxyiminoacetamido]ceph-3-em-4-carboxylate 1-Oxide (syn isomer)

t-Butyl hypochlorite (0.3ml) was added to a vigorously stirred solution of t-butyl (6R,7R)-3-carbamoyloyloxymethyl-7-[2-(fur-2-yl)-2-methoxyiminoacetamido]ceph-3-em-4-carboxylate (0.98 g) in pyridine (25 ml) and water (1 ml) at −45°. After stirring for 2 minutes, 2N sulphurous acid (1 ml) was added to the solution and the mixture was immediately poured into 20% w/v aqueous orthophosphoric acid (100 ml). The solution was extracted with ethyl acetate (2×100 ml), and the combined organic extracts were washed with aqueous NaHCO$_3$ (100 ml), and water (100 ml), and were then dried (M$_g$SO$_4$) and concentrated in vacuo.

The crude product was chromatographed on silica gel preparative plates, using ethyl acetate as eluant, the minor component of S-oxide running ahead of the R-oxide. Extraction of the slower component with ethyl acetate yielded the title compound (0.27 g, 27%).

IR and NMR data confirmed the structure as that of the title compound.

(c) (1R,6R,7R)-3-Carbamoyloxymethyl-7-[2-(fur-2-yl)-2-methoxyiminoacetamido]ceph-3-em-4-carboxylic Acid 1-Oxide (syn isomer)

t-Butyl (1R,6R,7R)-3-carbamoyloxymethyl-7-[2-(fur-2-yl)-2-methoxyiminoacetamido]ceph-3-em-4-carboxylate 1-oxide (syn isomer) (0.42 g) was dissolved in trifluoroacetic acid (5 ml) and stirred at room temperature for 8 minutes. The solution was evaporated to a red oil in vacuo, dissolved in ethyl acetate:acetone (1:1, 5 ml) and added dropwise with stirring to petroleum ether (60°-80°, 50 ml). The deposited solid was collected and dried in a desiccator. The crude product was slurried with ethyl acetate, and the liquid phase was decanted and added dropwise to petroleum ether (60°-80°, 50 ml), yielding the title compound as a colourless solid (150 mg, 40%), $\lambda_{max}$ (0.25N NaHCO$_3$) 263.5 ($\epsilon$ 15,000) and 281 nm ($\epsilon$ 13,700); $\nu_{max}$ (Nujol) 1,799 ($\beta$-lactam), 1725 and 1716 (COOH and OCONH$_2$), 1684 and 1538 (CONH) and 1060 and 1050 cm$^{-1}$ (S→O); $\tau$ (Me$_2$SO-d$_6$) values include 0.02 (d, J8Hz, CONH), 4.17(dd, J4 and 8Hz, 7-H), 4.99 (d, J4Hz, 6-H) and 6.09 (s, N-OCH$_3$).

Example 12

(1S,6R,7R)-3-Carbamoyloxymethyl-7-[2-(fur-2-yl)-2-methoxyiminoacetamido]ceph-3-em-4-carboxylic Acid 1-Oxide (syn isomer)

To a stirred solution of sodium (6R,7R)-3-carbamoyloxymethyl-7-[2-(fur-2-yl)-2-methoxyiminoacetamido]ceph-3-em-4-carboxylate (syn isomer) (2.59 g) in water (25 ml) was added sodium metaperiodate (1.93 g). The solution was stirred for 30 minutes at ambient temperature and then acidified by the dropwise addition of 2N aqueous hydrochloric acid. The resulting precipitate was collected, washed successively with water, ethanol and ether and then dried in vacuo to afford the title compound as a white powder (1.63 g.), $[\alpha]_D^{20}$ + 113° (c 0.86, Me$_2$SO); $\lambda_{max}$ (pH6 buffer) 264.5 ($\epsilon$ 17,200) and 279 nm ($\epsilon$ 15,600); $\nu_{max}$ (Nujol) 1779 ($\beta$-lactam), 1740 and 1716(CO$_2$H), 1688, 1654, 1589 and 1530 (CONH and OCONH$_2$) and 1030cm$^{-1}$ (S→O), $\tau$ (Me$_2$SO-d$_6$)0.60 (d, J 8Hz, NH), 2.11, 3.19, 3.31 (multiplets, furyl protons), 4.08 (q, J5 and 8Hz, C-7H). 4.87 and 5.45 (ABq, J13Hz, CH$_2$OCONH$_2$), 4.96(d, J 5Hz, C-6H), 6.08 (s, OCH$_3$), 6.10 and 6.42(ABq, J 18Hz, C-2 CH$_2$).

Example 13

(1R,6R,7R)-and(1S,6R,7R)-3-Carbamoyloxymethyl-7-[2-(fur-2-yl)-2-methoxyiminoacetamido]ceph-3-em-4-carboxylic Acid 1-Oxides (Syn isomers)

A solution of sodium periodate (1.93 g) in water (10 ml) was added to a stirred solution of sodium (6R,7R)-3-carbamoyloxymethyl-7-[2-(fur-2-yl)-2-methoxyiminoacetamido]ceph-3-em-4-carboxylate (2.59 g) in water (25 ml). Stirring was continued for 30 minutes at room temperature and the solution was then acidified with 2N HCl (2 ml). The deposited 1S-oxide was filtered off, washed with ethanol (5 ml) and ether (20 ml) and dried in a desiccator, yielding 1.59 g of colourless solid, $[\alpha]_D$ + 110° (c 1, Me$_2$SO), resembling the product described in Example 12.

The mother liquors were saturated with sodium chloride and filtered, and the filtrate was extracted with ethyl acetate (2×100 ml). The organic extracts were combined, dried (M$_g$SO$_4$) and concentrated in vacuo, yielding a yellow solid. The crude product was washed with acetone and the insoluble material was removed by filtration. The filtrate was evaporated to dryness and the acetone washing repeated yielding 380 mg of the 1R-oxide, $[\alpha]_D$ − 88° (c 1, Me$_2$SO), $\tau$ (Me$_2$SO-d$_6$) values similar to those reported in Example 11.

Example 14

(a) Diphenylmethyl (6R,7R)-3-Carbamoyloxymethyl-7-[2-(fur-2-yl)-2-phenoxyiminoacetamido]ceph-3-em-4-carboxylate (syn isomer)

A solution of DL-dicyclohexylcarbodiimide (7.75 g, 0.382 mole) in dry dichloromethane (50 ml) was added over 10 minutes to a solution of diphenylmethyl (6R,7R)-7-amino-3-carbamoyloxymethylceph-3-em-4- carboxylate (13.7 g, 0.312 mole) and 2-(fur-2-yl)-2-phenoxyiminoacetic acid (syn isomer) (8.8 g, 0.382 mole) in dry dichloromethane (200 ml) at 0°. After 45 minutes, a solid (presumably N,N'-dicyclohexyl urea) was filtered off, and the filtrate was washed with aqueous sodium bicarbonate solution and water, dried over magnesium sulphate, and evaporated on a rotary evaporator. The residue was chromatographed on a Silica gel (1 kg) column. Less polar impurities than the reqired product were eluted with dichloromethane (1 liter), acetone: dichloromethane=2:98 (1 liter), acetone:dichloromethane=5:95 (4 liters). Fractions eluted with acetone:dichloromethane=10:90 and acetone:dichloromethane=15:85 were evaporated to a gum (11 g) which was triturated with diethyl ether to give a solid (8.35 g, 41%). This was filtered off and purified further by crystallisation from aqueous ethanol to give the title compound (7.6 g), m.p. 143° to 146°; $[\alpha]_D^{22°} + 48°$ (c 1.0, Me$_2$SO); $\lambda_{max}^{EtOH}$ 273 nm ($\epsilon$ 18,700), $\lambda_{inf.}^{EtOH}$ 271 nm ($\epsilon$ 17,600) and $\lambda_{max}^{EtOH}$ 254 nm ($\epsilon$ 16,500).

IR, NMR and microanalytical data confirmed the structure as that of the title compound.

(b) Sodium (6R,7R)-3-Carbamoyloxymethyl-7-[2-(fur-2-yl)-2-phenoxyiminoacetamido]ceph-3-em-4-carboxylate (syn isomer)

Trifluoroacetic acid (30 ml) was added over 10 minutes to an ice-cooled mixture of anisole (8 ml) and diphenylmethyl (6R,7R)-3-carbamoyloxymethyl-7-[2-(fur-2-yl)-2-phenoxyiminoacetamido]ceph-3-em-4-carboxylate (syn isomer) (7.4 g, 11.4 mmole). After a further 5 minutes at 0°, the dark solution was carefully poured into a mixture of a saturated aqueous solution of sodium bicarbonate and ether acetate. The aqueous solution was separated and treated with activated charcoal. The ethyl acetate layer was washed with water and the aqueous wash was combined with the sodium bicarbonate extract and acidified with concentrated hydrochloric acid. This acidic solution was extracted with a mixture of ethyl acetate and diethyl ether which was then washed 5 times with water, dried over magnesium sulphate, and evaporated in vacuo. The residue was washed with diethyl ether and diisopropyl ether to give the cephalosporin acid (4.5 g, 82%) as a solid.

This acid was dissolved in ethyl acetate (150 ml) and a solution of sodium 2-ethylhexanoate in ethyl acetate (10 ml, containing 10 mmole) was added. The solution was cooled in an ice-bath and stirred for 1.5 hours during which time the product (2.84 g) crystallised out, leaving unchanged acid (1.1 g was recovered by precipitation with petrol b.p. 60° to 80°) in solution. The solid was filtered off to give the title compound.

Physical constants for the title compound are given in Table 1 hereinafter.

Example 15

(a) Diphenylmethyl (6R,7R)-3-Carbamoyloxymethyl-7-(2-methoxyimino-2-phenylacetamido)ceph-3-em-4-carboxylate (syn isomer)

Diphenylmethyl (6R,7R)-7-amino-3-carbamoyloxymethylceph-3-em-4-carboxylate p-toluenesulphonic acid salt (1.83 g, 3 mmole) was added to a mixture of saturated aqueous sodium bicarbonate solution (50 ml) and dichloromethane (100 ml). The mixture was shaken to dissolve the solid and the organic layer was separated, washed with water (twice), dried over sodium sulphate, and concentrated under reduced pressure to about 15 ml. This solution was cooled to 0° and solutions of D,L-dicyclohexylcarbodiimide (824 mg, 4 mmole) in dry dichloromethane (10 ml) and 2-methoxyimino-2-phenylacetic acid (syn isomer) (716 mg, 4 mmole) in dry dichloromethane (10 ml) were added. The reaction mixture was stirred at 0° for 70 minutes; it was then filtered, washed with 2N-sulphuric acid, water, saturated aqueous sodium bicarbonate solution, water and brine, dried over sodium sulphate and evaporated to give a yellow solid (2.05 g). This was dissolved in hot ethyl acetate (25 ml), which was cooled and dicyclohexyl urea was filtered off. Addition of diisopropyl ether to the filtrate precipitated a solid which was filtered off, stirred and washed with diisopropyl ether, filtered, and finally washed with diethyl ether to give the title compound (1.10 g, 61.5%), m.p. 178°–182°; $[\alpha]_D + 22.5°$ (c 1, CHCl$_3$); $\lambda_{max}^{EtOH}$ 258.5 nm ($\epsilon$ 18,500); $\lambda_{inf.}^{EtOH}$ 295 nm ($\epsilon$ 3,120).

IR, NMR and microanalytical data confirmed the structure as that of the title compound.

(b) (6R,7R)-3-Carbamoyloxymethyl-7-(2-methoxyimino-2-phenylacetamido)ceph-3-em-4-carboxylate Acid (syn isomer)

Treatment of the product of (a) above in accordance with the method of Example 1 (b) gave the title compound (75%), the compound being purified by trituration of the crude product with ethyl acetate (10 ml) followed by washing twice (with stirring) with diethyl ether (25 ml and 10 ml).

Physical constants for the title compound are given in Table 1 hereinafter.

Example 16

(a) Diphenylmethyl (6R,7R)-3-Carbamoyloxymethyl-7-(2-phenoxyimino-2-phenylacetamido)ceph-3-em-4-carboxylate (syn isomer)

The process of Example 15 (a) was repeated, except that 2-phenoxyimino-2-phenylacetic acid (syn isomer) was used in place of the 2-methoxyimino-2-phenylacetic acid (syn isomer), to give a red sticky foam. This crude product was crystallised from aqueous acetone to give a red solid (1.3 g) which was washed twice (with stirring) with diethyl ether to give the title compound (675 mg, 34%) m.p. 138°–140°; $[\alpha]_D + 44.5°$ (c 1, CHCl$_3$); $\lambda_{max}^{EtOH}$ 264 nm ($\epsilon$ 12,400); $\lambda_{inf.}^{EtOH}$ 268 and 281 nm ($\epsilon$ 16,850 and 14,000) as a white solid. The residue obtained after evaporating the mother liquors and washings was crystallised from ethanol to give further title compound (431 mg, 17%) in two crops, which were washed with diethyl ether with stirring.

IR, NMR and microanalytical data confirmed the structure as that of the title compound.

(b) Sodium (6R,7R)-3-Carbamoyloxymethyl-7-(2-phenoxyimino-2-phenylacetamido)ceph-3-em-4-carboxylate (syn isomer)

Treatment of the product of (a) above in accordance with the method of Example 1 (b) gave the crude cephalosporin acid, which was stirred with ethyl acetate and saturated aqueous sodium bicarbonate solution. The resulting precipitate was filtered off and washed with acetone and ether to give the title compound (66%), having the physical constants shown in Table 1 hereinafter.

Example 17

Diphenylmethyl (6R,7R)-3-Carbamoyloxymethyl-7-[2-cyclopentyloxyimino-2-(fur-2-yl)-acetamido]ceph-3-em-4-carboxylate (syn isomer)

The process of Example 15 (a) was repeated, except that 2-cyclopentyloxyimino-2-(fur-2-yl)acetic acid (syn isomer) was used in place of the 2-methoxyimino-2-phenylacetic acid (syn isomer) to give a foam (1.77 g), which was triturated with ethyl acetate to give the title compound (1.30 g, 67%), m.p. 102°–108°; $[\alpha]_D + 12.5°$ (c 1, CHCl$_3$); $\lambda_{max}^{EtOH}$ 278 nm ($\epsilon$ 16,650), as a pale-yellow solid.

(b) (6R,7R)-3-Carbamoyloxymethyl-7-[2-cyclopentyloxyimino-2-(fur-2-yl)acetamido]ceph-3-em-4-carboxylic Acid (syn isomer)

Treatment of the product of (a) above in accordance with the method of Example 1 (b) gave the crude cephalosporin acid, which was precipitated from ethyl acetate with diisopropyl ether to give the title compound (55%), having the physical constants shown in Table 1 hereinafter.

Example 18

(a) Diphenylmethyl (6R,7R)-3-Carbamoyloxymethyl-7-(2-ethoxyimino-2-phenylacetamido)ceph-3-em-4-carboxylate (syn isomer)

The process of Example 15 (a) was repeated, except that 2-ethoxyimino-2-phenylacetic acid (syn isomer) was used in place of the 2-methoxyimino-2-phenylacetic acid (syn isomer). Crystallisation of the crude product from methanol gave the title compound (1.30 g, 53%) in three crops, m.p. 199°–202°; $[\alpha]_D + 9.7°$ (c 1, dioxan); $\lambda_{max}^{EtOH}$ 259 nm ($\epsilon$ 20,000); $\lambda_{inf.}^{EtOH}$ 295 nm ($\epsilon$ 3,700).

(b) (6R,7R)-3-Carbamoyloxymethyl-7-(2-ethoxyimino-2-phenylacetamido)ceph-3-em-4-carboxylic Acid (syn isomer)

Treatment of the product of (a) above in accordance with the method of Example 1(b) gave the crude cephalosporin acid, which was triturated with ethyl acetate (3 ml), filtered off, and washed (with stirring) with ethyl acetate (5 ml) and then diethyl ether (2×10 ml) to give the title compound as a white solid (413 mg, 64%). A further quantity (180 mg, 27%) crystallised from the filtrates and was filtered off, and washed with diethyl ether. Physical constants for the title compound are shown in Table 1 hereinafter.

Example 19

(a) Diphenylmethyl (6R,7R)-3-Carbamoyloxymethyl-7-[2-t-butoxyimino-2-(thien-2-yl)-acetamido]ceph-3-em-4-carboxylate (syn isomer)

The process of Example 15 (a) was repeated, except that 2-t-butoxyimino-2-(thien-2yl)acetic acid (syn isomer) was used in place of the 2-methoxyimino-2-phenylacetic acid (syn isomer). The crude product was purified by stirring a suspension in diisopropyl ether (2×25 ml) to give the title compound as a pale-pink solid (1.90 g, 73%), m.p. 148°–152°; $[\alpha]_D + 8.5°$ (c 1, CHCl$_3$); $\lambda_{max}^{EtOH}$ 262 and 282 nm ($\epsilon$ 14,500 and 13,200).

(b) Sodium (6R,7R)-3-Carbamoyloxymethyl-7-[2-t-butoxyimino-2-(thien-2-yl)acetamido]ceph-3-em-4-carboxylate (syn isomer)

Treatment of the product of (a) above in accordance with the method of Example 1(b) gave the cephalosporin acid as a gum which solidified when triturated with diisopropyl ether to give a crude product (1.20 g, 94%). A portion of this acid (811 mg, 1.68 mmole) and sodium 2-ethylhexanoate (282 mg, 1.68 mmole) were stirred in n-butanol (5 ml) at 20° for 10 minutes and at 0° for 20 minutes. The resulting yellow solid was filtered off and washed with cold n-butanol (3 ml) and diisopropyl ether (7 ml) to give the title compound (495 mg, 58%), having the physical constants shown in Table 1 hereinafter.

Table 1

Physical properties of the products of Examples 14 – 19

| Example No. | $[\alpha]_D$ (solvent) | $R_{PAC}^{(1)}$ (solvent system) | pH6$^{(2)}$ $\lambda_{max}$ ($\epsilon$) (nm) | $\nu_{max}$ (cm$^{-1}$) in Nujol | | | | | | |
|---|---|---|---|---|---|---|---|---|---|---|
| | | | | NH$_2$ | NH | COOH | $\beta$-lactam | CONH | COOH | CONH | COO$^-$ |
| 14 (b) | + 89° (Me$_2$SO) | 1.1 (A) | 298 (15,000) 270 (16,700) | 3350 | | 3270 | 1765 | 1710 1715 | — | 1690 1530 | 1630 |
| 15 (b) | + 56° (dioxan) | 1.0 (B) | 260 (18,900) | 3490 | 3440 | 3370 3270 | 1760 | 1724 | 1700 | 1650 1527 | — |
| 16 (b) | + 129° (Me$_2$SO) | 1.1(A) 1.2(B) | 262 (18,200) 266.5 (17,600)inf 280 (13,200)inf | 3450 | 3340 | 3260 3210 | 1740 | 1690 | — | 1653 1533 1672 | 1605 |
| 17 (b) | + 64° (Me$_2$SO) | 1.0 (A) | 275.5 (17,200) | 3700 | — | 2100 | 1783 | 1718 1724 | 1716 | 1530 1652 | — |
| 18 (b) | + 68° (EtOH) | 1.05 (A) | 259.5(19,200) | 3480 | 3440 | 3280 3370 | 1763 | | 1700 1658 | 1524 | — |
| 19 (b) | + 53° (H$_2$O) | 1.1 (B) | 262 (15,050) 289 (10,500)inf | 3450 | 3335 | 3370 | 1750 | 1690 | — | 1520 | 1610 |

| | $\tau$ (in Me$_2$SO-d$_6$) | | | | | | |
|---|---|---|---|---|---|---|---|
| Example No. | NH d J 8Hz | NH$_2$ | C$_7$–H dd J 5,8Hz | C$_6$–H d J 5Hz | C$_3$–CH$_2$ ABq J 13Hz | C$_2$–H q J 18Hz | Side chain Aromatic (m) Aliphatic |
| | | | | | 5.00 | 6.40 | 1.98 |

Table 1-continued

Physical properties of the products of Examples 14 – 19

| | | | | | | | | |
|---|---|---|---|---|---|---|---|---|
| 14 (b) | −0.10 | 3.43 | 4.23 | 4.85 | 5.27 | | 2.35–3.02 3.22 | |
| 15 (b) | 0.23 | 3.4 | 4.11 | 4.74 | 5.07 5.34 | 6.40 | 2.1–2.7 | 6.04 (s) |
| 16 (b) | (3) 1.72 | — | 3.82 | 4.61 | 4.53 4.87 5.02 | 6.13 6.40 | 1.9– 2.9 2.12 | |
| 17 (b) | 0.29 | 3.4 | 4.14 | 4.77 | 5.32 | 6.41 | 3.3– 3.4 | 5.78 7.9– 8.7 (m) |
| 18 (b) | 0.22 | 3.4 | 4.08 | 4.73 | 5.09 5.33 | 6.31 6.52 | 2.0– 3.0 | 5.76 (q J 7Hz) 8.70 (J 7Hz) |
| 19 (b) | 0.41 | 3.48 | 4.34 | 4.94 | 5.16 | 6.56 | 2.42 2.03 2.92 | 8.68 (s) |

| Example No. | Microanalysis (%) Found/calc. | | | | Empirical formula (solvent present) |
|---|---|---|---|---|---|
| | C | H | N | S | |
| 14 (b) | 48.2 | 3.8 | 10.5 | 5.9 | $C_{21}H_{17}N_4SO_8$ |
| | 48.2 | 3.6 | 10.7 | 6.1 | (1 mole $H_2O$) |
| 15 (b) | 50.1 | 4.3 | 12.4 | 7.2 | $C_{18}H_{18}N_4SO_7$ |
| | 49.8 | 4.2 | 12.9 | 7.4 | |
| 16 (b) | 49.5 | 3.65 | 9.6 | 5.8 | $C_{23}H_{19}N_4SO_7Na$ |
| | 49.9 | 4.15 | 10.0 | 5.8 | (2 moles $H_2O$) |
| 17 (b) | 50.6 | 5.4 | 10.5 | | $C_{20}H_{22}N_4SO_8$ |
| | 51.8 | 5.2 | 10.8 | | [0.4 mole (i-$Pr)_2O$] |
| 18 (b) | 52.6 | 4.3 | 11.9 | 7.1 | $C_{19}H_{20}N_4SO_7$ |
| | 52.2 | 4.3 | 11.9 | 6.8 | (0.2 mol anisole) |
| 19 (b) | | | | | $C_{19}H_{21}N_4S_2O_7Na$ |

Notes $$^{(1)}R_{pac} = \frac{(R_f \text{ of compound})}{(R_f \text{ of (6R,7R)-3-acetoxymethyl-7-phenylacetamidoceph-3-em-4-carboxylic acid})}$$

Solvent system (A) is n-butanol: ethanol: water (4:1:5)
Solvent system (B) is n-propanol: water (7:3)
$^{(2)}$inf. denotes an inflection
$^{(3)}$Trifluoroacetic acid spectrum

(c) EXAMPLES OF PHARMACEUTICAL COMPOSITIONS

Example A

Dry Powder for Injection

The sterile sodium (6R, 7R)-3-carbamoyloxymethyl-7-[2-(fur-2-yl)-2-methoxyiminoacetamido]ceph-3-em-4-carboxylate(syn isomer) is filled into glass vials, the claimed contents of each container being 500 mg and 1.00 g of the cephalosporin compound. Filling is carried out aseptically under a blanket of nitrogen. The vials are closed using rubber discs or plugs held in position by aluminum sealing rings, thereby preventing gaseous exchange or ingress of micro-organisms. The product is intended for reconstitution with Water for Injections or other suitable sterile vehicle shortly before administration.

Example B

Intramammary Injection (for Cattle)

| Percentage Composition (w/w) | |
|---|---|
| Sodium (6R, 7R)-3-carbamoyloxymethyl-7-[2-(fur-2-yl)-2-methoxyiminoacetamido]ceph-3-em-4-carboxylate (syn isomer) | 8.33 |
| Vehicle to: | 100.00 |
| Vehicle: Tween 60 | 3.00 |
| White Beeswax | 6.00 |
| Arachis Oil | 91.00 |

The last three ingredients are heated together at 150° for one hour and then cooled to room temperature with stirring. The sterile antibiotic, finely powdered, is added aseptically to this vehicle and the product refined with a high speed mixter. The preparation is filled aseptically into sterile collapsible aluminium tubes with a fill weight of 3.0 g, each tube containing 250 mg of the cephalosporin compound. The product is intended for administration into the mammary gland through the test canal.

We claim:

1. A compound selected from the group consisting of a cephalosporin antibiotic of the formula

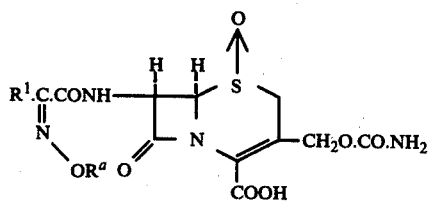

wherein $R^1$ is furyl, thienyl, or phenyl; and $R^a$ is $C_{1-4}$ alkyl, $C_{3-7}$ cycloalkyl or phenyl; and a physiologically acceptable salt thereof.

2. The compound of claim 1 which is (1R,6R,7R)-3-carbamoyloxymethyl-7-[2-(fur-2-yl)-2-methoxyiminoacetamido]ceph-3-em-4-carboxylic acid 1-oxide (syn isomer).

3. The compound of claim 1 which is (1S,6R,7R)-3-carbamoyloxymethyl-7-[2-(fur-2-yl)-2-methoxyiminoacetamido]ceph-3-em-4-carboxyic acid 1-oxide (syn isomer).

* * * * *

UNITED STATES PATENT OFFICE
CERTIFICATE OF CORRECTION

Patent No. 4,138,555  Dated February 6, 1979

Inventor(s) Martin C. Cook, Gordon I. Gregory and Janice Bradshaw

It is certified that error appears in the above-identified patent and that said Letters Patent are hereby corrected as shown below:

In column 1 of the title page, line 4 from the bottom, "May 12, 1972 [GB] United Kingdom . . . 45884/72" should read --August 21, 1973 [GB] United Kingdom . . . . 39645/73--.

Signed and Sealed this

Nineteenth Day of June 1979

[SEAL]

Attest:

RUTH C. MASON
*Attesting Officer*

DONALD W. BANNER
*Commissioner of Patents and Trademarks*